(12) United States Patent
Terpetschnig et al.

(10) Patent No.: US 7,411,068 B2
(45) Date of Patent: Aug. 12, 2008

(54) LUMINESCENT COMPOUNDS

(76) Inventors: Ewald A. Terpetschnig, 1704B Trails Dr., Urbana, IL (US) 61802; Anatoliy Tatarets, Geroev Truda Street, Building 48D, Flat 24, Kharkov (UA) 61135; Olga Galkina, Rybalko Street, Building 20, Flat 90, Kharkov (UA) 61091; Iryna Fedyunyaeva, Mira Street, Building 20, Flat 14, Kharkov (UA) 61007; Leonid Patsenker, 23-Avgusta Street, Building 41, Flat 24, Kharkov (UA) 61103

( * ) Notice: Subject to any disclaimer, the term of this patent is extended or adjusted under 35 U.S.C. 154(b) by 320 days.

(21) Appl. No.: 10/986,446

(22) Filed: Nov. 10, 2004

(65) Prior Publication Data

US 2005/0202565 A1 Sep. 15, 2005

Related U.S. Application Data

(63) Continuation-in-part of application No. 10/724,580, filed on Nov. 28, 2003, now Pat. No. 7,250,517, which is a continuation-in-part of application No. 10/396,293, filed on Mar. 24, 2003, now abandoned, and a continuation-in-part of application No. PCT/US03/10995, filed on Apr. 10, 2003, said application No. 10/396,293 is a continuation-in-part of application No. 09/684,627, filed on Oct. 6, 2000, now Pat. No. 6,538,129, which is a continuation-in-part of application No. PCT/US99/07627, filed on Apr. 7, 1999.

(60) Provisional application No. 60/371,832, filed on Apr. 10, 2002, provisional application No. 60/083,820, filed on May 1, 1998.

(51) Int. Cl.
C07D 215/12 (2006.01)
G01N 21/76 (2006.01)
C12Q 1/68 (2006.01)

(52) U.S. Cl. .................... 546/176; 435/6; 436/172; 546/176

(58) Field of Classification Search ................ 546/176; 436/172; 435/6
See application file for complete search history.

(56) References Cited

U.S. PATENT DOCUMENTS

| | | | |
|---|---|---|---|
| 3,996,345 A | 12/1976 | Ullman et al. | |
| 3,998,943 A | 12/1976 | Ullman | |
| 4,883,867 A | 11/1989 | Lee et al. | |
| 5,101,015 A | 3/1992 | Brynes et al. | |
| 5,227,499 A | 7/1993 | McGowan et al. | |
| 5,571,388 A | 11/1996 | Patonay et al. | |
| 6,083,485 A | 7/2000 | Licha et al. | |
| 6,140,494 A | 10/2000 | Hamilton et al. | |
| 6,403,807 B1 | 6/2002 | Singh et al. | |
| 6,538,129 B1 * | 3/2003 | Terpetschnig et al. ...... 536/26.6 |
| 2003/0026763 A1 | 2/2003 | Licha et al. | |

FOREIGN PATENT DOCUMENTS

| WO | WO 96/41144 | 12/1996 |
|---|---|---|
| WO | WO 97/40104 | 10/1997 |

OTHER PUBLICATIONS

Synthesis and Characterization of Unsymmetrical Squaraines: A New Class of Cyanine Dyes, Terpetschnig et al., *Dyes and Pigments*, vol. 21, pp. 227-234, 1993.

Synthesis, spectral properties and photostabilities of symmetrical and unsymmetrical squaraines; a new class of fluorophores with long-wavelength excitation and emission, Terpetschnig et al., *Analytica Chimica Acta*, vol. 282, pp. 633-641, 1993.

Synthesis of Squaraine-N-Hydroxysuccinimide Esters and Their Biological Application as Long-Wavelength Fluorescent Labels, Terpetschnig et al., *Analytical Biochemistry*, vol. 217, pp. 197-204, 1994.

Synthesis, Spectral Properties, and Detection Limits of Reactive Squaraine Dyes, a New Class of Diode Laser Compatible Fluorescent Protein Labels, Oswald et al., *Bioconjugate Chem.*, vol. 10, pp. 925-931, 1999.

Red Laser-Induced Fluorescence Energy Transfer in an Immunosystem, Oswald et al., *Analytical Biochemistry*, vol. 280, pp. 272-277, 2000.

* cited by examiner

Comparsion of the relative intensities of the Di-sulfo-NH-squaraine dyes (15) of this invention and the conventional Di-sulfo-sqaraine dye (3b).

*Primary Examiner*—Jezia Riley
(74) *Attorney, Agent, or Firm*—Kolisch Hartwell, P.C.

(57) ABSTRACT

The invention provides reporter compounds based on squaric, croconic, and/or rhodizonic acid, among others, reactive intermediates used to synthesize the reporter compounds, and methods of synthesizing and using the reporter compounds, among others.

The reporter compounds relate generally to the following structure

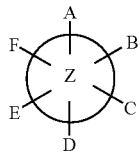

Here, Z is a four, five, or six-member aromatic ring, and A, B, C, D, E, and F are substituents of Z, where F is absent when Z is a five-member ring, and where E and F are absent when Z is a four-member ring.

A, B, C, D, E, and F are selected from a variety of elements and groups, including but not necessarily limited to O, S, Se, Te, N—$R^a$, $C(R^b)(R^c)$, $W^1$, and $W^2$.

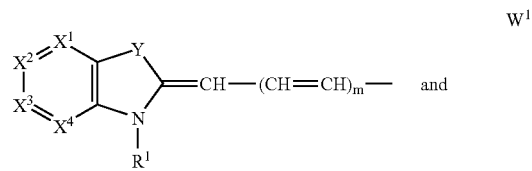

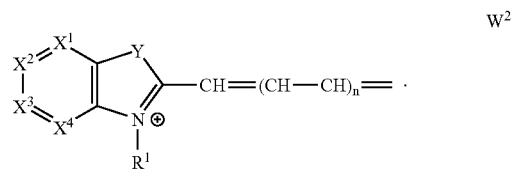

29 Claims, 4 Drawing Sheets

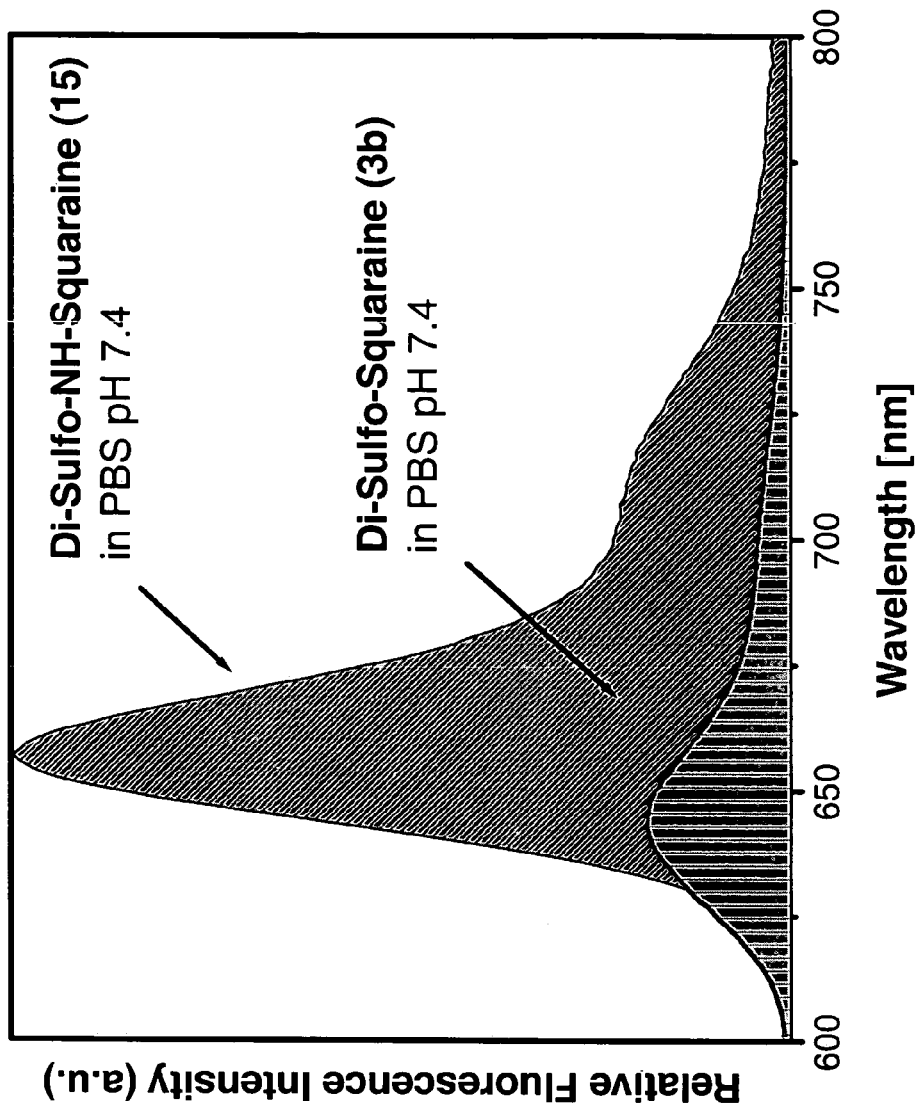
Figure 1. Comparsion of the relative intensities of the Di-sulfo-NH-squaraine dyes (15) of this invention and the conventional Di-sulfo-sqaraine dye (3b).

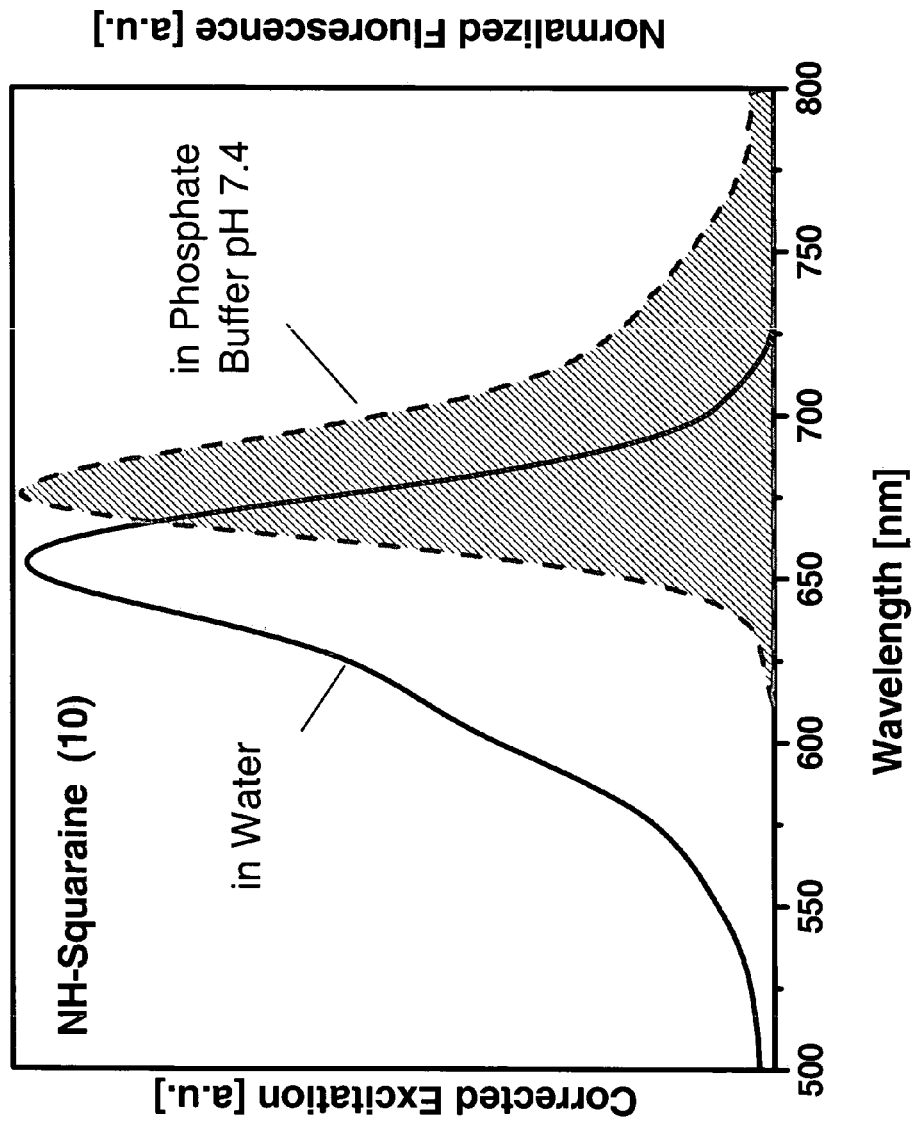
Figure 2. provides the absorption (in water) and the emission spectrum (in PBS) of the mono-NH squaraine dye 10.

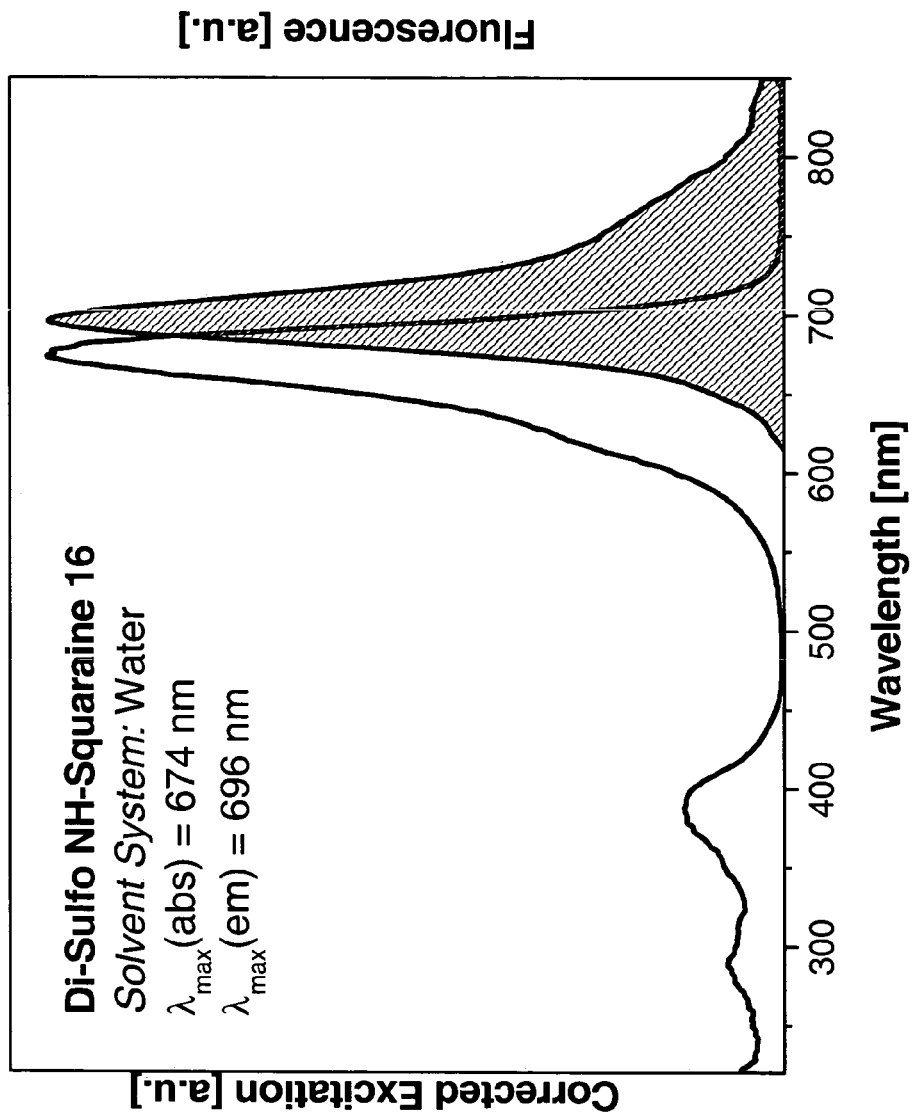
Figure 3. Plot of the absorption and emission spectrum of the Di-sulfo-NH-squaraine 16 in water.

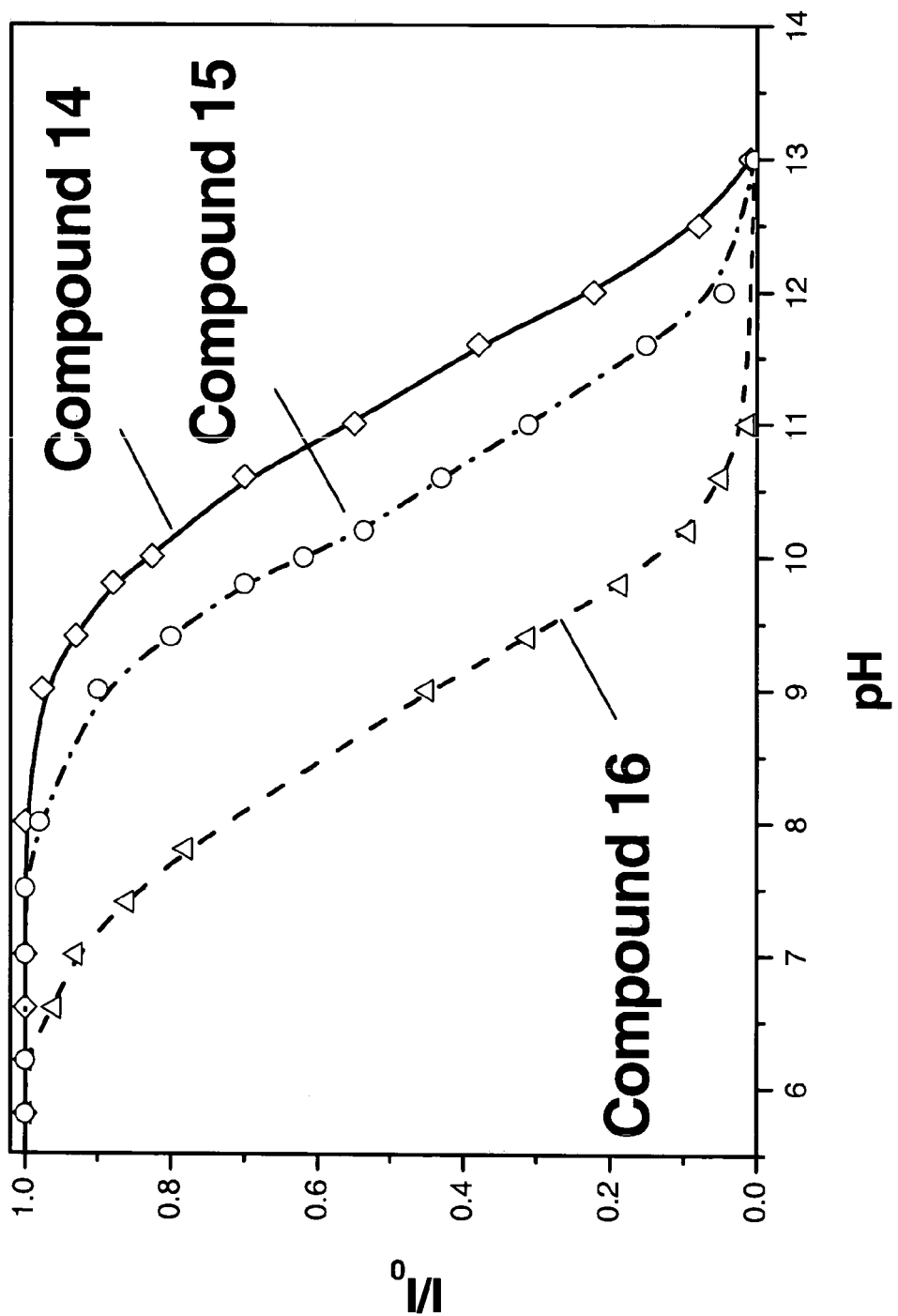
Figure 4. Plot of the pH titration curves for compounds 14, 15 and 16.

LUMINESCENT COMPOUNDS

CROSS-REFERENCES TO PRIORITY APPLICATIONS

This application is a continuation-in-part of U.S. patent application Ser. No. 10/724,580, filed Nov. 28, 2003 now U.S. Pat. No. 7,250,517.

U.S. patent application Ser. No.10/724,580, in turn, is a continuation-in-part of the following patent applications: U.S. patent application Ser. No. 10/396,293, filed Mar. 24, 2003 now abandoned; and PCT patent application Ser. No. PCT/US03/10995, filed Apr. 10, 2003.

U.S. patent application Ser. No. 10/396,293, in turn, is a continuation-in-part of U.S. patent application Ser. No. 09/684,627, filed Oct. 6, 2000, now U.S. Pat. No. 6,538,129, which is a continuation of PCT patent application Ser. No. PCT/US99/07627, filed Apr. 7,1999, which is based upon and claims the benefit under 35 U.S.C. § 119(e) and all other applicable national and international law of the following patent applications: Deutsches Patentamt Application Serial No. 198 15 659.6, filed Apr. 8, 1998 in the German Patent Office, entitled REAKTIVE QUADRATSÄUREUND CROCONSÄURE-FARBSTOFFE ALS MARKER FÜR BIOMOLEKÜLE UND ARZNEISTOFFE, and naming Ewald Terpetschnig as inventor; and U.S. Provisional Patent Application Ser. No. 60/083,820, filed May 1, 1998. U.S. patent application Ser. No. 10/396,293 also is based upon and claims the benefit under 35 U.S.C. § 119(e) of U.S. Provisional Patent Application Ser. No. 60/371,832, filed Apr. 10, 2002.

PCT patent application Ser. No. PCT/US03/10995, in turn, is based upon and claims the benefit under 35 U.S.C. § 119(e) and all other applicable national and international law of U.S. Provisional Patent Application Ser. No. 60/371,832, filed Apr. 10, 2002.

Each of the above-identified U.S., PCT, foreign, and provisional priority patent applications is incorporated herein by reference in its entirety for all purposes.

CROSS-REFERENCE TO RELATED MATERIAL

This application incorporates by reference in their entirety for all purposes all patents, patent applications (published, pending, and/or abandoned), and other patent and nonpatent references cited anywhere in this application. The cross-referenced materials include but are not limited to the following publications: Richard P. Haugland, HANDBOOK OF FLUORESCENT PROBES AND RESEARCH CHEMICALS (6th ed. 1996); JOSEPH R. LAKOWICZ, PRINCIPLES OF FLUORESCENCE SPECTROSCOPY (2nd Ed. 1999); RICHARD J. LEWIS , SR., HAWLEY'S CONDENSED CHEMICAL DICTIONARY (12th ed. 1993).

TECHNICAL FIELD

The invention relates to compounds based on squaric, croconic, and/or rhodizonic acid, among others. More particularly, the invention relates to compounds based on squaric, croconic, and/or rhodizonic acid, among others, that are useful as dyes and luminescent reporters.

BACKGROUND

Colorimetric and/or luminescent compounds may offer researchers the opportunity to use color and light to analyze samples, investigate reactions, and perform assays, either qualitatively or quantitatively. Generally, brighter, more photostable reporters may permit faster, more sensitive, and more selective methods to be utilized in such research.

While a calorimetric compound absorbs light, and may be detected by that absorbance, a luminescent compound, or luminophore, is a compound that emits light. A luminescence method, in turn, is a method that involves detecting light emitted by a luminophore, and using properties of that light to understand properties of the luminophore and its environment. Luminescence methods may be based on chemiluminescence and/or photoluminescence, among others, and may be used in spectroscopy, microscopy, immunoassays, and hybridization assays, among others.

Photoluminescence is a particular type of luminescence that involves the absorption and subsequent re-emission of light. In photoluminescence, a luminophore is excited from a low-energy ground state into a higher-energy excited state by the absorption of a photon of light. The energy associated with this transition is subsequently lost through one or more of several mechanisms, including production of a photon through fluorescence or phosphorescence.

Photoluminescence may be characterized by a number of parameters, including extinction coefficient, excitation and emission spectrum, Stokes' shift, luminescence lifetime, and quantum yield. An extinction coefficient is a wavelength-dependent measure of the absorbing power of a luminophore. An excitation spectrum is the dependence of emission intensity upon the excitation wavelength, measured at a single constant emission wavelength. An emission spectrum is the wavelength distribution of the emission, measured after excitation with a single constant excitation wavelength. A Stokes' shift is the difference in wavelengths between the maximum of the emission spectrum and the maximum of the absorption spectrum. A luminescence lifetime is the average time that a luminophore spends in the excited state prior to returning to the ground state. A quantum yield is the ratio of the number of photons emitted to the number of photons absorbed by a luminophore.

Luminescence methods may be influenced by extinction coefficient, excitation and emission spectra, Stokes' shift, and quantum yield, among others, and may involve characterizing fluorescence intensity, fluorescence polarization (FP), fluorescence resonance energy transfer (FRET), fluorescence lifetime (FLT), total internal reflection fluorescence (TIRF), fluorescence correlation spectroscopy (FCS), fluorescence recovery after photobleaching (FRAP), and their phosphorescence analogs, among others.

Luminescence methods have several significant potential strengths. First, luminescence methods may be very sensitive, because modern detectors, such as photomultiplier tubes (PMTs) and charge-coupled devices (CCDs), can detect very low levels of light. Second, luminescence methods may be very selective, because the luminescence signal may come almost exclusively from the luminophore.

Despite these potential strengths, luminescence methods may suffer from a number of shortcomings, at least some of which relate to the luminophore. For example, the luminophore may have an extinction coefficient and/or quantum yield that is too low to permit detection of an adequate amount of light. The luminophore also may have a Stokes' shift that is too small to permit detection of emission light Without significant detection of excitation light. The luminophore also may have an excitation spectrum that does not permit it to be excited by wavelength-limited light sources, such as common lasers and arc lamps. The luminophore also may be unstable, so that it is readily bleached and rendered nonluminescent. The luminophore also may have an excitation and/or emission spectrum that overlaps with the well-known autoluminescence of biological and other samples; such autoluminescence is particularly significant at wavelengths below about 600 nm. The luminophore also may be expensive, especially if it is difficult to manufacture.

SUMMARY

The invention provides reporter compounds based on squaric, croconic, and/or rhodizonic acid, among others, reactive intermediates used to synthesize the reporter compounds, and methods of synthesizing and using the reporter compounds, among others.

The reporter compounds relate generally to the following structure:

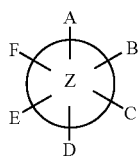

Here, Z is a four, five, or six-member aromatic ring, and A, B, C, D, E, and F are substituents of Z, Where F is absent when z is a five-member ring, and where E and F are absent when Z is a four-member ring. Generally, A, B, C, D, E, and F may be present in any order, although the order may be limited in certain embodiments.

A, B, C, D, E, and F are selected from a variety of elements and groups, including but not necessarily limited to O, S, Se, Te, $N-R^a$, $C(R^b)(R^c)$, $W^1$, and $W^2$.

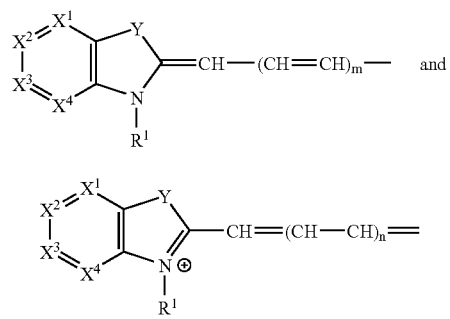

The components $R^a$, $R^b$, $R^c$, $R^d$, $R^e$, $R^f$, $R^i$, $R^j$, -L-$S_c$, -L-$R^x$, -L-$R^\pm$, —$R^x$, —$R^\pm$, n, m, $X^1$, $X^2$, $X^3$, $X^4$, and Y are defined in detail in the Detailed Description. However, generally, each compound includes at least one of $W^1$ or $W^2$, with the preferred synthetic precursors including one, and the preferred reporter compounds including two. The compound may include at least one H in $R^1$. Alternatively, or in addition, the compound may include at least one atom at $X^1$ through $X^4$ of $W^1$ or $W^2$. Alternatively, or in addition, the compound may include one or more ionic groups —$R^\pm$ in combination with a reactive group —$R^x$ or a carrier —$S_c$. Alternatively, or in addition, A, B, C, D, E, and F may be chosen so that the compound is photoluminescent.

The methods relate generally to the synthesis and/or use of reporter compounds, especially those described above.

The nature of the invention will be understood more readily after consideration of the drawing, chemical structures, and detailed description that follow.

BRIEF DESCRIPTION OF THE DRAWINGS

FIG. 1. Comparison of the relative intensities of the Di-sulfo-NH-squaraine dyes (15) of this invention and the conventional Di-sulfo-sqaraine dye (3b).

FIG. 2. Provides the absorption (in water) and the emission spectrum (in PBS) of the mono-NH squaraine dye 10.

FIG. 3. Plot of the absorption and emission spectrum of the Di-sulfo-NH-squaraine 16 in water.

FIG. 4. pH titration curves (I/Io) vs. pH for compounds 14, 15 and 16.

| Abbreviations The following abbreviations, among others, may be used in this application: | |
|---|---|
| Abbreviation | Definition |
| BSA | bovine serum albumin |
| Bu | butyl |
| DCC | dicyclohexylcarbodiimide |
| DMF | dimethylformamide |
| D/P | dye-to-protein ratio |
| Et | ethyl |
| g | grams |
| h | hours |
| HSA | human serum albumin |
| hCG | human chorionic gonadotropin |
| L | liters |
| m | milli ($10^{-3}$) |
| M | molar |
| Me | methyl |
| mol | moles |
| M.P. | melting point |
| n | nano ($10^{-9}$) |
| NHS | N-hydroxysuccinimide |
| NIR | near infrared region |
| PBS | phosphate-buffered saline |
| Prop | propyl |
| TMS | tetramethylsilane |
| TSTU | N,N,N',N'-tetramethyl(succinimido)uronium tetra-fluoroborate |
| μ | micro ($10^{-6}$) |

DETAILED DESCRIPTION OF THE INVENTION

The invention relates generally to photoluminescent compounds and their synthetic precursors, and to methods of synthesizing and using such compounds. These photoluminescent compounds may be useful in both free and conjugated forms, as probes, labels, and/or indicators. This usefulness may reflect in part enhancement of one or more of the following: quantum yield, Stokes' shift, extinction coefficients, and photostability. This usefulness also may reflect excitation and emission spectra in relatively inaccessible regions of the spectrum, including the red and near infrared.

The remaining discussion includes (1) an overview of structures, (2) an overview of synthetic methods, and (3) a series of illustrative examples.

Overview of Structures

The reporter compounds and their synthetic precursors may be generally described by the following structure:

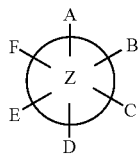

Here, Z is a four, five, or six-member aromatic ring, and A, B, C, D, E, and F are substituents of Z, where F is absent if Z is a five-member ring, and where E and F are absent if Z is a six-member ring. A, B, C, D, E, and F may be singly or doubly bonded to Z.

Ring Z may take a variety of forms. Preferred rings are based on four-member squaric acid, five-member croconic acid, and six-member rhodizonic acid, and/or their analogs, with substitutions as described below.

Substituents A, B, C, D, E, and F also may take a variety of forms. Preferred substituents include O, S, Se, Te, N—$R^a$, $C(R^b)(R^c)$, $W^1$, and $W^2$. $R^a$, $R^b$, and $R^c$ may be selected from the group consisting of aliphatic, heteroatom-substituted aliphatic, polyether, aromatic, reactive aliphatic, and reactive aromatic groups, among others.

$W^1$ and $W^2$ may include the following structures, among others:

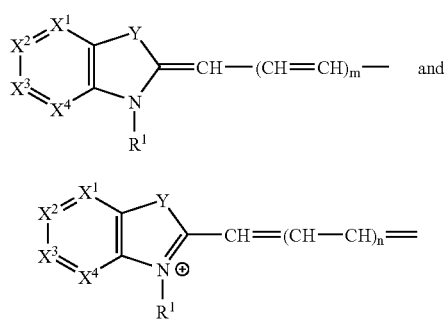

For each of $W^1$ and $W^2$, the variables n, m, Y, $R^1$, and $X^1$ through $X^4$ generally may be defined independently, as follows. The integers n and m may independently be 0, 1, or 2. Y may be O, S, Se, Te, N—$R^d$, $CR^e$=$CR^f$ and $C(R^i)(R^j)$. $R^d$ may be H, aliphatic groups, alicyclic groups, aromatic groups, and reactive aliphatic groups, among others. $R^e$, $R^f$, $R^i$ and $R^j$ may be H, aliphatic, -L-$R^x$, -L-$R^\pm$, —$CH_2$—CONH—$SO_2$-Me, among others.

-L- is a single covalent bond, a covalent linkage that is linear or branched, cyclic or heterocyclic, saturated or unsaturated, having 1-20 nonhydrogen atoms from the group of C, N, P, O and S, in such a way that the linkage contains any combination of ether, thioether, amine, ester, amide bonds; single, double, triple or aromatic carbon-carbon bonds; or carbon-sulfur bonds, carbon-nitrogen bonds, phosphorus-sulfur, nitrogen-nitrogen, nitrogen-oxygen or nitrogen-platinum bonds, or aromatic or heteroaromatic bonds;

$R^x$ is a reactive group;

$S_c$ is a conjugated substance;

$R^\pm$ is an ionic group;

$R^1$ is selected from H, -L-$S_c$, -L-$R^x$, -L-$R^\pm$, —$CH_2$—CONH—$SO_2$-Me, aliphatic groups, among others, provided that at least one of $R^1$ in the entire molecule is H.

Finally, ring members $X^1$, $X^2$, $X^3$, and $X^4$ may be selected from the group consisting of N, N$R^\iota$, O, S, and C—$R^\tau$, where $R^\iota$ is hydrogen, -L-$S_c$, -L-$R^x$, -L-$R^\pm$, —$CH_2$—CONH—$SO_2$-Me, alkyl, arylalkyl and aryl groups, among others; $R^\tau$ is H, -L-$S_c$, -L-$R^x$, —L-$R^\pm$, —$R^x$, —$R^\pm$, —$CH_2$—CONH—$SO_2$-Me, amino, alkylamino, dialkylamino, trialkylammonium, sulfo, trifluoromethyl, alkoxy, halogen, carboxy, hydroxy, phosphate, sulfate or an aliphatic, alicyclic, or aromatic group; adjacent $R^\iota$ and/or $R^\tau$ substituents, taken in combination, form a fused aromatic or heterocyclic ring that is itself optionally further substituted. The substituents on these condensed rings may be chosen quite broadly, and may include the various components listed above, among others.

Reporter Compounds

Where the reporter compound is a colorimetric dye and/or a photoluminescent compound, B and C are typically chosen from $W^1$ and/or $W^2$, and A, B, C, D, E, and F typically are present in any order. If B and C are adjacent, then each of B and C is $W^1$, and each of A, D, E, and F is neutral. If B and C are separated by one of A, D, E, or F, then one of B and C is $W^1$, one of B and C is $W^2$, and one of A, D, E, and F is negatively charged. If B and C are separated by two of A, D, E, and F, which is possible only in the six-member ring, then each of B and C is $W^2$, and each of A, D, E, and F is neutral.

Representative structures for the reporter compounds are shown below, where $W^1$ and $W^2$ represent the structures defined above, and where $V^1$ through $V^4$ represent the structures A, D, E, and F as defined above, in any order.

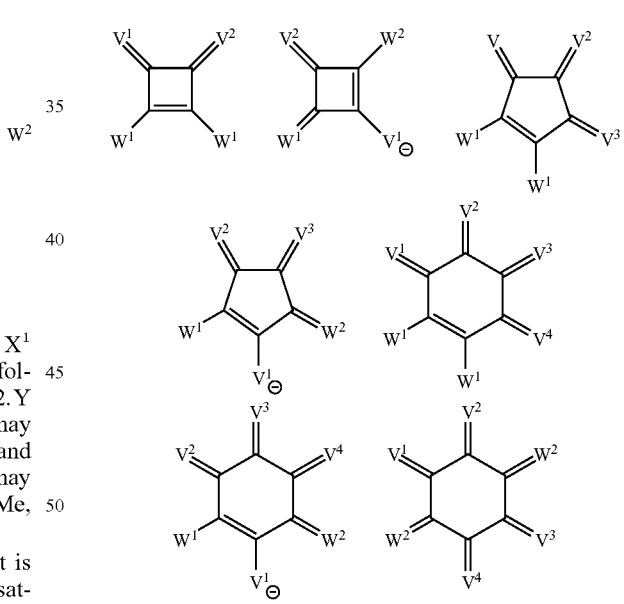

Depending on the embodiment, A, B, C, D, E, and F may be subject to additional limitations. In some embodiments, the compound also includes at least one of O, S, Se, Te, N—$R^a$ and $C(R^b)(R^c)$. In other embodiments, at least one of $X^1$ through $X^4$ of $W^1$ or $W^2$ is or includes a heteroatom. In yet other embodiments, the compound may include a reactive group and/or a carrier. The reporter compounds may be calorimetric dyes, useful as stains and for colorimetric detection. Alternatively or in addition, the reporter compounds may be photoluminescent, particularly fluorescent, and may have utility in photoluminescence assays and methods, as discussed above.

Synthetic Precursors.

Where the compound has utility as a synthetic precursors, B typically is one of $W^1$ and $W^2$, and C is analogous to D, E, and F. A representative precursor in which Z is a four-member ring is shown below.

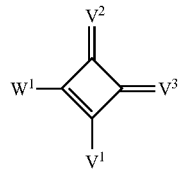

Here, $V^1$ may be $O^-$, $S^-$, OH, SH, OR, SR, NRH, NRR (where each R is independently methyl, ethyl, i-propyl, butyl, among others); and $[C(R')(R')]^-$, among others, where each R' may be CN, COOH, C(=O)NHR, COOEt, $COOCH_3$, among others. $V^2$ and $V^3$ may be O, S, NR, and CRR, among others, where each R may be CN, COOH, C(=O)NHR, and COOEt, aliphatic and aromatic groups, among others.

Analogous precursors in which Z is a five or six-member ring also may be useful as synthetic precursors. Examples of selected compounds and their synthetic routes are shown below:

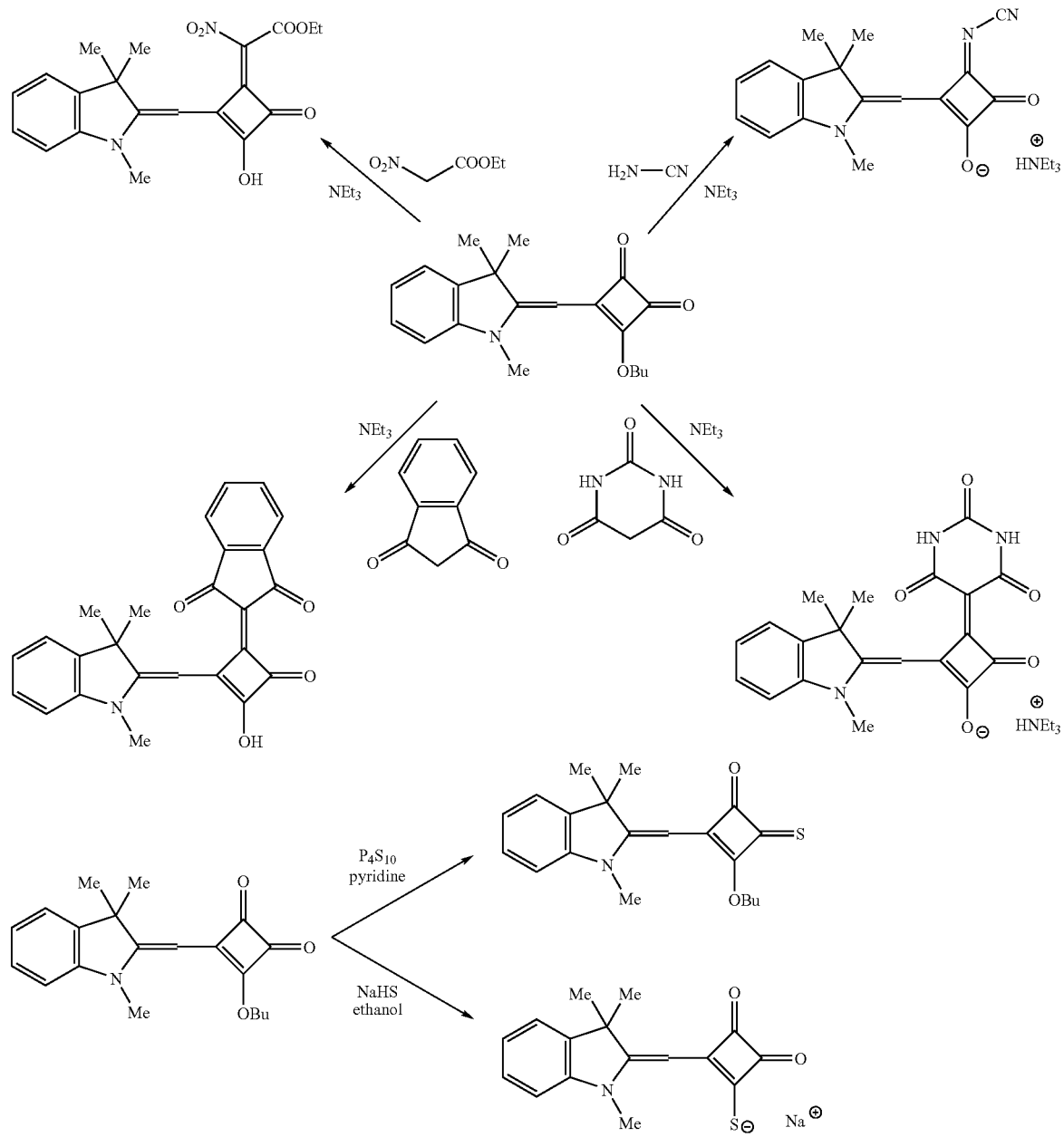

Any of these precursors can be reacted with a second heterocyclic compound to generate an unsymmetrical NH-squaraine dye.

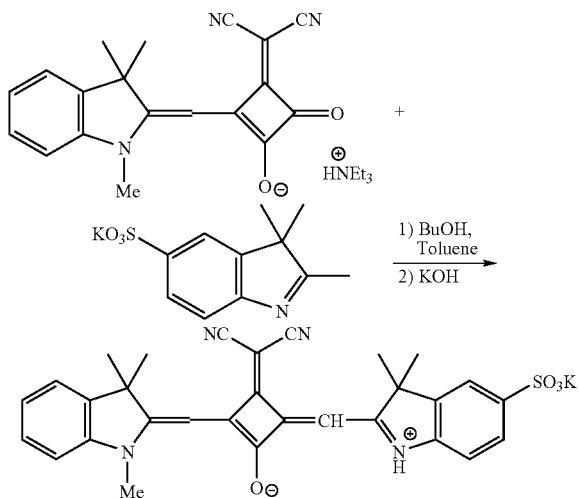

Tandems.

Reporter compounds in accordance with the invention also may include pairs, triplets, and higher numbers of compounds conjugated together to form a single compound. Such "tandems" may be used to obtain alternative spectral properties, such as enhanced Stokes' shifts. Such tandems also may be used in energy transfer, or for other purposes. Some potential combinations are drawn below, where A, B, C, D, E, F, and Z have their usual meanings, and U represents a cross-link, such as may be formed by cross-reaction using a reactive compound. Z and each substituent may be chosen independently for each component of a tandem.

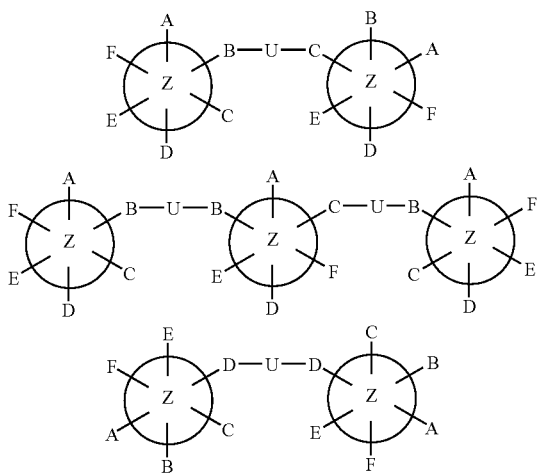

Reactive Groups ($R^x$).

The substituents of Z may include one or more reactive groups, where a reactive group generally is a group capable of forming a covalent attachment with another molecule or substrate. Such other molecules or substrates may include proteins, carbohydrates, nucleic acids, and plastics, among others. Reactive groups ($R^x$) vary in their specificity, and may preferentially react with particular functional groups and molecule types. Thus, reactive compounds generally include reactive groups chosen preferentially to react with functional groups found on the molecule or substrate with which the reactive compound is intended to react.

The compounds of the invention are optionally substituted, either directly or via a substituent, by one or more chemically reactive functional groups that may be useful for covalently attaching the compound to a desired substance. Each reactive group $R^x$, may be bound to the compound directly by a single covalent bond (—$R^x$), or may be attached via a covalent spacer or linkage, -L-, and may be depicted as -L-$R^x$.

The reactive group (—$R^x$) of the invention may be selected from the following functional groups, among others: activated carboxylic esters, acyl azides, acyl halides, acyl halides, acyl nitrites, acyl nitrites, aldehydes, ketones, alkyl halides, alkyl sulfonates, anhydrides, aryl halides, azindines, boronates, carboxylic acids, carbodiimides, diazoalkanes, epoxides, haloacetamides, halotriazines, imido esters, isocyanates, isothiocyanates, maleimides, phosphoramidites, silyl halides, sulfonate esters, and sulfonyl halides.

The following reactive functional groups (—$R^x$), among others, are particularly useful for the preparation of labeled molecules or substances, and are therefore suitable reactive functional groups for the purposes of the reporter compounds:

a) N-hydroxysuccinimide esters, isothiocyanates, and sulfonylchlorides, which form stable covalent bonds with amines, including amines in proteins and amine-modified nucleic acids;
b) Iodoacetamides and maleimides, which form covalent bonds with thiol-functions, as in proteins;
c) Carboxyl functions and various derivatives, including N-hydroxybenztriazole esters, thioesters, p-nitrophenyl esters, alkyl, alkenyl, alkynyl, and aromatic esters, and acyl imidazoles;
d) Alkylhalides, including iodoacetamides and chloroacetamides;
e) Hydroxyl groups, which can be converted into esters, ethers, and aldehydes;
f) Aldehydes and ketones and various derivatives, including hydrazones, oximes, and semicarbozones;
g) Isocyanates, which may react with amines;
h) Activated C=C double-bond-containing groups, which may react in a Diels-Alder reaction to form stable ring systems under mild conditions;
i) Thiol groups, which may form disulfide bonds and react with alkylhalides (such as iodoacetamide);
j) Alkenes, which can undergo a Michael addition with thiols, e.g., maleimide reactions with thiols;
k) Phosphoramidites, which can be used for direct labeling of nucleosides, nucleotides, and oligonucleotides, including primers on solid or semi-solid supports;
l) Primary amines that may be coupled to variety of groups including carboxyl, aldehydes, ketones, and acid chlorides, among others; and
m) Boronic acid derivatives that may react with sugars.

R Groups

The R moieties associated with the various substituents of Z may include any of a number of groups, as described above, including but not limited to aliphatic groups, alicyclic groups, aromatic groups, and heterocyclic rings, as well as substituted versions thereof.

Aliphatic groups may include groups of organic compounds characterized by straight- or branched-chain arrangement of the constituent carbon atoms. Aliphatic hydrocarbons comprise three subgroups: (1) paraffins (alkanes), which are saturated and comparatively unreactive; (2) olefins (alkenes or alkadienes), which are unsaturated and quite reactive; and (3) acetylenes (alkynes), which contain a triple bond and are highly reactive. In complex structures, the chains may be branched or cross-linked and may contain one or more heteroatoms (such as polyethers and polyamines, among others).

As used herein, "alicyclic groups" include hydrocarbon substituents that incorporate closed rings. Alicyclic substituents may include rings in boat conformations, chair conformations, or resemble bird cages. Most alicyclic groups are derived from petroleum or coal tar, and many can be synthesized by various methods. Alicyclic groups may optionally include heteroalicyclic groups, that include one or more heteroatoms, typically nitrogen, oxygen, or sulfur. These compounds have properties resembling those of aliphatics and should not be confused with aromatic compounds having the hexagonal benzene ring. Alicyclics may comprise three subgroups: (1) cycloparaffins (saturated), (2) cycloolefins (unsaturated with two or more double bonds), and (3) cycloacetylenes (cyclynes) with a triple bond. The best-known cycloparaffins (sometimes called naphthenes) are cyclopropane, cyclohexane, and cyclopentane; typical of the cycloolefins are cyclopentadiene and cyclooctatetraene. Most alicyclics are derived from petroleum or coal tar, and many can be synthesized by various methods.

Aromatic groups may include groups of unsaturated cyclic hydrocarbons containing one or more rings. A typical aromatic group is benzene, which has a 6-carbon ring formally containing three double bonds in a delocalized ring system. Aromatic groups may be highly reactive and chemically versatile. Most aromatics are derived from petroleum and coal tar. Heterocyclic rings include closed-ring structures, usually of either 5 or 6 members, in which one or more of the atoms in the ring is an element other than carbon, e.g., sulfur, nitrogen, etc. Examples include pyridine, pyrole, furan, thiophene, and purine. Some 5-membered heterocyclic compounds exhibit aromaticity, such as furans and thiophenes, among others, and are analogous to aromatic compounds in reactivity and properties.

Any substituent of the compounds of the invention, including any aliphatic, alicyclic, or aromatic group, may be further substituted one or more times by any of a variety of substituents, including without limitation, F, Cl, Br, I, carboxylic acid, sulfonic acid, CN, nitro, hydroxy, phosphate, phosphonate, sulfate, cyano, azido, amine, alkyl, alkoxy, trialkylammonium or aryl. Aliphatic residues can incorporate up to six heteroatoms selected from N, O, S. Alkyl substituents include hydrocarbon chains having 1-22 carbons, more typically having 1-6 carbons, sometimes called "lower alkyl".

As described in WO01/11370, sulfonamide groups such as —$(CH_2)_n$—$SO_2$—NH—$SO_2$—R, —$(CH_2)_n$—CONH—$SO_2$—R, —$(CH_2)_n$—$SO_2$—NH—CO—R, and —$(CH_2)_n$—$SO_2$NH—$SO_3$H, where R is aryl or alkyl and n=1-6, can be used to reduce the aggregation tendency and have positive effects on the photophysical properties of cyanines and related dyes, in particular when these functional groups are directly associated with the benzazole ring in position 1 (the nitrogen atom in the azole ring).

Where a substituent is further substituted by a functional group $R^{\pm}$ that is ionically charged, such as for example a carboxylic acid, sulfonic acid, phosphoric acid, phosphonate or a quaternary ammonium group, the ionic substituent $R^{\pm}$ may serve to increase the overall hydrophilicity of the compound.

As used herein, functional groups such as "carboxylic acid," "sulfonic acid," and "phosphoric acid" include the free acid moiety as well as the corresponding metal salts of the acid moiety, and any of a variety of esters or amides of the acid moiety, including without limitation alkyl esters, aryl esters, and esters that are cleavable by intracellular esterase enzymes, such as alpha-acyloxyalkyl ester (for example acetoxymethyl esters, among others).

The compounds of the invention are optionally further substituted by a reactive functional group $R^x$, or a conjugated substance $S_c$, as described below.

The compounds of the invention may be depicted in structural descriptions as possessing an overall charge, it is to be understood that the compounds depicted include an appropriate counter ion or counter ions to balance the formal charge present on the compound. Further, the exchange of counter ions is well known in the art and readily accomplished by a variety of methods, including ion-exchange chromatography and selective precipitation, among others.

Carriers and Conjugated Substances $S_c$

The reporter compounds of the invention, including synthetic precursor compounds, may be covalently or noncovalently associated with one or more substances. Covalent association may occur through various mechanisms, including a reactive functional group as described above, and may involve a covalent linkage, -L-, separating the compound or precursor from the associated substance (which may therefore be referred to as -L-$S_c$).

A covalent linkage binds the reactive group $R^x$, the conjugated substance $S_c$ or the ionic group $R^{\pm}$ to the dye molecule, either directly via a single covalent bond which is depicted in the text as —$R^x$, —$R^{\pm}$, —$S_c$, or with a combination of stable chemical bonds (-L-), that include single, double, triple or aromatic carbon-carbon bonds; carbon-sulfur bonds, carbon-nitrogen bonds, phosphorus-sulfur bonds, nitrogen-nitrogen bonds, nitrogen-oxygen or nitrogen-platinum bonds, or aromatic or heteroaromatic bonds; -L- includes ether, thioether, carboxamide, sulfonamide, urea, urethane or hydrazine moieties. Preferably, -L- includes a combination of single carbon-carbon bonds and carboxamide or thioether bonds.

Where the substance is associated noncovalently, the association may occur through various mechanisms, including incorporation of the compound or precursor into or onto a solid or semisolid matrix, such as a bead or a surface, or by nonspecific interactions, such as hydrogen bonding, ionic bonding, or hydrophobic interactions (such as Van der Walls forces). The associated carrier may be selected from the group consisting of polypeptides, polynucleotides, polysaccharides, beads, microplate well surfaces, metal surfaces, semiconductor and non-conducting surfaces, nanoparticles, and other solid surfaces.

The associated or conjugated substance may be associated with or conjugated to more than one reporter compound, which may be the same or different. Generally, methods for the preparation of dye-conjugates of biological substances are well-known in the art. See, for example, Haugland et al., MOLECULAR PROBES HANDBOOK OF FLUORESCENT PROBES AND RESEARCH CHEMICALS, Eighth Edition (1996), or G. T. Hermanson, Bioconjugate Techniques, Academic Press, London, (1996), which is hereby incorporated by reference. Typically, the association or conjugation of a chromophore or luminophore to a substance imparts the spectral properties of the chromophore or luminophore to that substance.

Useful substances for preparing conjugates according to the present invention include, but are not limited to, amino acids, peptides, proteins, phycobiliproteins, nucleosides, nucleotides, nucleic acids, carbohydrates, lipids, ion-chelators, biotin, pharmaceutical compounds, nonbiological polymers, cells, and cellular components. The substance to be conjugated may be protected on one or more functional groups in order to facilitate the conjugation, or to insure subsequent reactivity.

Where the substance is a peptide, the peptide may be a dipeptide or larger, and typically includes 5 to 36 amino acids. Where the conjugated substance is a protein, it may be an enzyme, an antibody, lectin, protein A, protein G, hormones, or a phycobiliprotein. The conjugated substance may be a nucleic acid polymer, such as for example DNA oligonucleotides, RNA oligonucleotiues (or hybrids thereof), or single-stranded, double-stranded, triple-stranded, or quadruple-stranded DNA, or single-stranded or double-stranded RNA.

Another class of carriers includes carbohydrates that are polysaccharides, such as dextran, heparin, glycogen, starch and cellulose.

Where the substance is an ion chelator, the resulting conjugate may be useful as an ion indicator (calcium, sodium, magnesium, Zinc, potassium and other important metal ions) particularly where the optical properties of the reporter-conjugate are altered by binding a target ion. Preferred ion-complexing moieties are crown ethers (U.S. Pat. No. 5,405,957) and BAPTA chelators (U.S. Pat. No. 5,453,517).

The associated or conjugated substance may be a member of a specific binding pair, and therefore useful as a probe for the complementary member of that specific binding pair, each specific binding pair member having an area on the surface or in a cavity which specifically binds to and is complementary with a particular spatial and polar organization of the other. The conjugate of a specific binding pair member may be useful for detecting and optionally quantifying the presence of the complementary specific binding pair member in a sample, by methods that are well known in the art.

Representative specific binding pairs may include ligands and receptors, and may include but are not limited to the following pairs: antigen-antibody, biotin-avidin, biotin-streptavidin, IgG-protein A, IgG-protein G, carbohydrate-lectin, enzyme-enzyme substrate; ion-ion-chelator, hormone-hormone receptor, protein-protein receptor, drug-drug receptor, DNA-antisense DNA, and RNA-antisense RNA.

Preferably, the associated or conjugated substance includes proteins, carbohydrates, nucleic acids, drugs, and nonbiological polymers such as plastics, metallic nanoparticles such as gold, silver and carbon nanostructures among others. Further carrier systems include cellular systems (animal cells, plant cells, bacteria). Reactive dyes can be used to label groups at the cell surface, in cell membranes, organelles, or the cytoplasm.

Finally these compounds can be linked to small molecules such as amino acids, vitamins, drugs, haptens, toxins, and environmental pollutants, among others. Another important ligand is tyramine, where the conjugate is useful as a substrate for horseradish peroxidase. Additional embodiments are described in U.S. patent application Publication No. US 2002/0077487.

Synthetic Methods, Characterization and Description of Preferred Embodiments

The synthesis of the disclosed reporter compounds is performed in a multi-step reaction, starting with the synthesis of a methylene base and a bridging unit. The syntheses of suitable bases may proceed based on literature or novel methods. Generally, the spectral properties of the reporter compounds, including excitation and emission wavelengths for luminescent compounds, may be strongly dependent on the type of methylene base used.

Preferred starting materials that include benzindoles, benzoselenzoles, benzoxazoles, benzimidazoles, or quinolines etc., and squaric acid or substituted versions thereof are described in Example 1. Some of these starting materials such as 1d-1g contain a reactive group or an ionic substituent and spacer groups in position 3 of the indolenine ring. The introduction of spacer groups in position 3 and/or increasing the number of ionic groups may help to reduce the tendency of the dyes to aggregate in aqueous solution and when covalently bound to proteins.

Squaric acid is a dibasic acid that undergoes a series of nucleophilic substitution reactions with various reagents, including amines, phenols, and CH-acidic compounds such as 1,2,3,3-tetramethyl-benzindole. The squaraine bridge in the resulting compounds stabilizes the conjugated chain and shifts the excitation and emission wavelength of these dyes to the red as compared to cyanine-based dyes.

The following examples describes the synthesis and spectral characterization of several long-wavelength reporter compounds based on NH-containing squaraine dyes, and some of their reactive derivatives. These dyes may include a cyanine-type chromophore and a bridge (squarate, croconium). For water-solubility, sulfonic acid or other groups including quaternary ammonium, polyether, sulfonamide, carboxyl, and phosphate, among others, may be introduced into the dye molecule. In order to facilitate covalent attachment to a variety of different biomolecules, reactive N-hydroxy-succinimide ester (NHS ester) or other reactive forms as described in U.S. patent application Publication No. 2002/0077487 may be synthesized.

The dyes of this invention show absorption and emission maxima starting at about 500 to beyond 800 nm and the absorption and emission wavelengths of the reporter compounds may be tuned by Substitution of the squaraine ring, Introducing heteroatoms into the heterocyclic moiety and Increasing the length of the conjugated carbon chain.

The substitution of C=O by C=C or C=S in the central squaraine ring as shown in compounds 9, 10, 16 acid 18 results in a bathochromic shift of both, the absorption and the emission spectra of these dyes. The absorption and emission properties can also be shifted by modification of the heterocyclic bases. The absorption wavelength for squaraines increases in the order indolenine<benzothiazolium<benzoselenzolium~quionoline. Sulfo-indolenine based squaraines (where A is =S ) absorb around 630 nm to 640 nm in water and at approximately 640 nm to 650 nm when bound to proteins or organic solvents. The emission maxima for benzothiazole-based squaraine dyes in organic solvents are around 680 nm to 690 nm and beyond 700 nm for benzoselenzole and quinoline derivatives.

In one example (Example 4), an unsymmetric dioxo-NH-squaraine dye (8) was synthesized and compared to the dioxo-N-alkyl-squaraine dye (8a) as described by Terpetschnig et al., Anal. Chem. Acta, 282 (1993), 633. 8 has an 8-nm larger Stokes' shift as compared to the unsymmetrical dye 8a.

8 was further reacted with $P_4S_{10}$ using pyridine as solvent. The absorption and emission spectral properties of the di-thio-NH compound 9 were clearly distinguishable from those of the parent di-oxo-derivative 8. The exchange of oxygen to sulfur in dye 9 led to an even higher increase of the Stokes' shift, resulting in a total shift of 37 nm. An increased Stokes' shift results in increased sensitivity in fluorescence measurements, due to better separation of the absorption and emission maxima, permitting the molecules to be excited closer to their absorbance maximum with higher extinction coefficients.

| Compound in CHCl$_3$ | $\lambda_{max}$ (abs) | $\lambda_{max}$ (em) | Stokes' Shift $\Delta\lambda$ |
| --- | --- | --- | --- |
| 8 | 666 | 692 | 26 |
| 8a | 657 | 675 | 18 |
| 9 | 687 | 724 | 37 |

| Squaraine | R | X |
| --- | --- | --- |
| 8 | H | O |
| 8a | CH$_3$ | O |
| 9 | H | S |

In general squaraine dyes are known to exhibit lower quantum yields in water ($\phi$=0.01-0.15) and high quantum yields ($\phi$=0.2-0.8) in organic solvents or in aqueous solution when bound to biomolecules. In one aspect of the invention the squaraine dyes contain two NH substitued indolenines (R$^1$ is H). A comparison of the fluorescent properties of a conventional reactive, water-soluble squaraine dye such as 3b (Example 2) and the reactive NH dye analog 15 (Example 7) as well as the NH dye 14 (Example 6) should help to depict the surprising and non-obvious features of NH-substituted dyes:

The chemical structures of dyes 3b, 14, and 15 is very similar. While both 3b and 15 are reactive and symmetrical 5-sulfo-substituted squaraine dyes, compound 14 is a non-reactive dye. The main difference between 3b and 15 can be found in the placement of the reactive hexanoic acid linker, which is at position 1 in the symmetrical squaraine 3b and at position 3 in the NH dye 15 leaving position 1 unsubstituted. Surprisingly the NH dyes 14 and 15 have very different photophysical properties as compared to 3b (see Table below and FIG. 1):

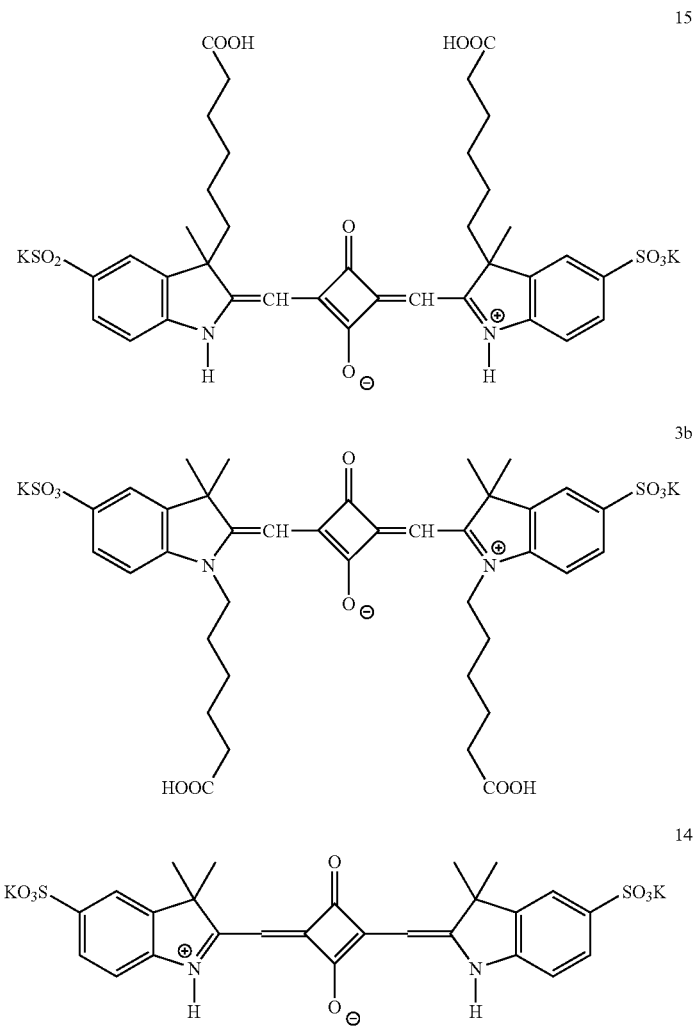

| Compound | $\lambda_{max}$ (abs) | $\lambda_{max}$ (em) | Solvent | Stokes' Shift $\Delta\lambda$ | Rel. Intensity [a.u.] |
|---|---|---|---|---|---|
| 3b | 635 | 642 | PBS | 7 | 60 |
| 14 | 638 | 654 | PBS | 16 | 300 |
| 15 | 640 | 657 | PBS | 17 | 330 |

While the absorption and emission wavelengths of these dyes are similar, 3b exhibits a Stokes' shift of only 7 nm, whereas the NH compounds 14 and 15 have a Stokes' shift of 16-17 nm. Moreover, compounds 14 and 15 are approximately 5 times brighter in water than compound 3b. Increased brightness and Stokes' shifts are desirable features for fluorescent labels because they both permit enhanced detection, and therefore allow for a more sensitive measurement technique. In addition larger Stokes' shifts help to reduce the self-quenching tendencies of such dyes when covalently labeled to proteins.

The substitution of one oxygen in the central squarate bridge by CH-acidic reagents e.g. dicyanomethane, HOOC—(CH$_2$)—COOH, or ROOC—(CH$_2$)—CN, leads to a group of luminescent methylenesquaraine derivatives. As compared to di-oxo squaraines these compounds have red-shifted excitation and emission properties and larger Stokes' shifts. In water the absorption and emission maxima of the representative reactive NH-dye 16 (Example 8) were found to be at 674 nm and 696 nm, respectively.

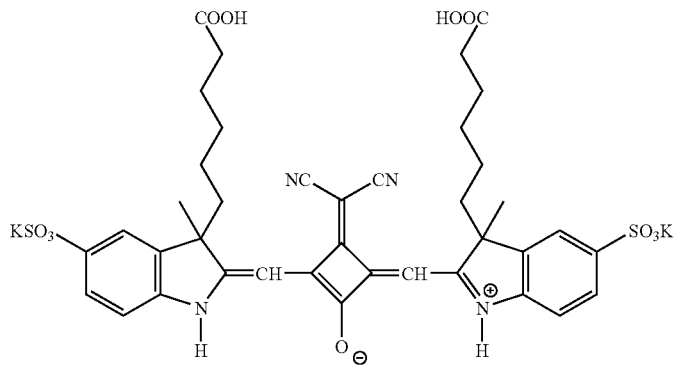

16

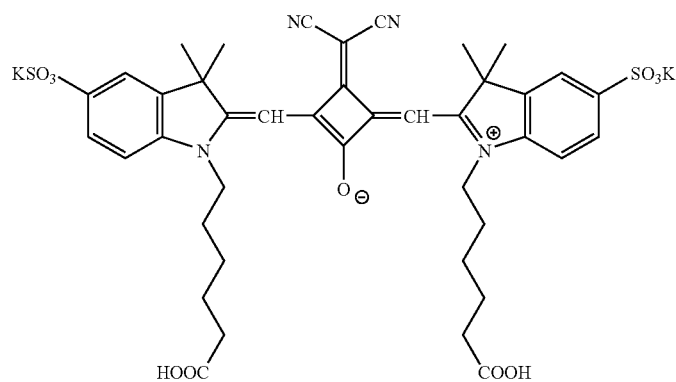

17

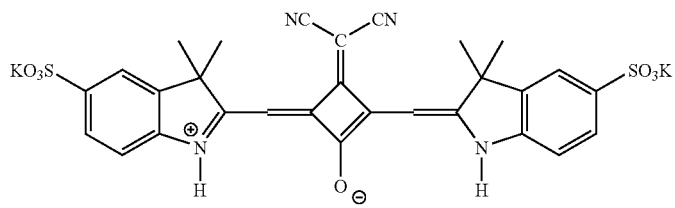

18

-continued

| Compound | λ<sub>max</sub> (abs) | λ<sub>max</sub> (em) | Solvent | Stokes' Shift Δλ | Rel. Intensity [a.u.] |
|---|---|---|---|---|---|
| 16 | 674 | 697 | PBS | 22 | 195 |
| 17 | 667 | 685 | PBS | 18 | 65 |
| 18 | 671 | 690 | PBS | 19 | 175 |

A comparison of the relative intensities of the NH-dicyanomethylene squaraine dye 16 and 18 (Example 10) with the conventional squaraine dye 17 (Example 9) indicates that the NH substituted derivatives are about 3 times as bright and also have a larger Strokes' shift. The data confirms the general trend of NH squaraine dyes having considerably higher Q.Y.'s and larger Stokes' shifts in aqueous solution in comparison to conventional N-alkylated squaraines. In addition the fluorescence lifetimes of the NH dyes 15 and 16 were measured to be approximately 2 ns in water (see Example 14), which is one of the longest lifetimes measured for red emitting cyanine dyes. The fluorescence lifetimes of such dyes are typically in the range between 0.01 ns to 1 ns [V. Buschmann et al., Bioconjugate Chem. 2003, 14, 195-204]. The longer fluorescence lifetime makes these dyes in particular valuable as labels in fluorescent polarization assays where the lifetime of the fluorophore can be considered an important criteria for its performance as a polarization label (E. Terpetschnig et al., Anal. Biochem. 227, 140-147,1995).

ILLUSTRATIVE EXAMPLES

Example 1

Synthesis of Precursors

This section describes the synthesis of various precursors. p-hydrazinobenzenesulfonic acid (Illy et al., J. Org. Chem. 33, 4283-4285 1968), 1-(5-carboxypentyl)-2,3,3-trimethyl-3H-5-indoliumsulfonate (1a), 2,3,3-trimethylindole-5-sulfonic acid potassium salt (1b), 1-(3-sulfonato propyl)-2,3,3-trimethylindoleninium-5-sulfonate (1h) (Mujumdar et al., Bioconj. Chem. 4(2) 105-111, 1993), and 1,2,3,3-tetramethylindoleninium-5-sulfonate (1c) were synthesized using literature procedures. 1d -1f are synthesized according to the procedures provided in U.S. patent application Publication No. 2002/0077487. 1-(2-phosphonethyl)-2,3,3-trimethylindoleninium-5-sulfonate (1i) is described in PCT Patent Application Publication No. WO 01/36973. Other starting materials such p-hydranzino-phenylacetic acid and the relevant indolenine are described in Southwick et al., Cytometry 11, 418-430 (1990). Finally, starting materials for cationic dyes containing quaternary ammonium residues (trimethyl or triethyl ammonium) can be synthesized according to Hamilton et al. U.S. Pat. No. 6,140,494.

The synthesis of 7-(carboxypentyl)-2,3,3-trimethyl-3H-pyrrolo[2,3-b]pyridin and 5-bromo-7-(3-sulfopropyl)-2,3,3-trimethyl-3H-pyrrolo[2,3-b]pyrimidinium starting materials for the synthesis of the relevant squaraine dyes is described in U.S. Patent Application No. 2002/0077487.

1,3-Dithiosquaric acid disodium salt (2c) and triethylammonium 2-butoxy-3-dicyanomethylene-4-oxo-1-cyclobuten-1-olate (2d) were synthesized according to Seitz et al. Chem. Ber. 112, 990-999, (1979) and Gerecht et al., Chem. Ber. 117, 2714-2729 (1984), respectively.

The 3-cyanoimino-4-oxo-1-cyclobutene-1,2-diolate (2e) is synthesized starting from dibutylsquarate according to the procedure of K. Köhler et al. Chem. Ber. 118, 1903-1916 (1985). Disodium-3,4-dioxo-1-cyclobutene-1,2-dithiolate trihydrate 2f is synthesized according to R. West, JOC 41(24), 3904 (1976) or G. Seitz et al., Chem. Ber. 112, 90-999 (1979).

Synthesis of 1-(5-carboxypentyl)-2,3,3-trimethyl-3H-5-indoliumsulfonate (1a) p-Hydrazinobenzenesulfonic acid 33 g of sodium carbonate was added to a suspension of 104 g (0.6 mol) of p-aminobenzenesulfonic acid in 400 mL of hot water. The solution was cooled to 5° C. in an ice-bath, and 70 g of concentrated sulfuric acid were added slowly under rapid stirring. A solution of 42 g of sodium nitrite in 100 mL of water was then added under cooling. A light yellow diazo-compound precipitate formed, which was filtered and washed with water, but not dried.

The wet diazo-compound was added under stirring and cooling (5° C.) to a solution of 170 g of sodium sulfite in 500 mL of water. The solution, which turned orange, was stirred under cooling for 1 h, and then heated to reflux. Finally, 400 mL of concentrated hydrochloric acid were added. The solution turned yellow, and the product precipitated as a white solid. For complete decoloration, 1-2 g of powdered zinc were added. The reaction mixture was cooled overnight, and the precipitate was filtered, washed with water, and dried in an oven at 100° C.

Yield: 96 g (85%), white powder; M.P.=286° C. (Lit.=285° C.); R<sub>f</sub>: 0.95 (RP-18, water:MeOH 2:1).

Synthesis of potassium 2,3,3-trimethylindoleninium-5-sulfonate (1b)

18.2 g (0.12 mol) of p-hydrazinobenzenesulfonic acid and 14.8 g (0.17 mol) of isopropylmethylketone were stirred in 100 mL of glacial acetic acid at room temperature for 1 h. The mixture was then refluxed for 4 h. The mixture was cooled to room temperature, and the resulting pink solid precipitate was filtered and washed with ether.

The precipitate was dissolved in methanol, and a concentrated solution of potassium hydroxide in 2-propanol was added until a yellow solid completely precipitated. The precipitate was filtered, washed with ether, and dried in a desiccator over $P_2O_5$.

Yield: 20.4 g (71%), off-white powder; M.P.=275° C.; R<sub>f</sub>: 0.40 (silica gel, isopropanol:water:ammonia 9:0.5:1).

1-(5-carboxypentyl)-2,3,3-trimethyl-3H-5-indoliumsulfonate (1a)

15.9 g (57 mmol) of potassium 2,3,3-trimethylindoleninium-5-sulfonate and 12.9 g (66 mmol) of 6-bromohexanoic acid were refluxed in 100 mL of 1,2-dichlorobenzene for 15 min under a nitrogen atmosphere. The solution was cooled to room temperature, and the resulting pink precipitate was filtered, washed with chloroform, and dried.

Yield: 15.8 g (58%), pink powder; R<sub>f</sub>: 0.75 (RP-18, MeOH:water 2:1).

Synthesis of 1,2,3,3-tetramethylindolium-5-sulfonate (1c)

1.1 g of 2,3,3-trimethylindoleninium-5-sulfonate were suspended in 30 mL of methyl iodide. The reaction mixture was heated to boiling for 25 h in a sealed tube. After the mixture was cooled, excess methyl iodide was decanted, and the residue was suspended in 50 mL of acetone. The solution was filtered, and the residue was dried in a desiccator over $CaCl_2$. The resulting light yellow powder was used without further purification.

Yield: 90%, light yellow powder.

Synthesis of 3-(5-carboxypentyl)-2,3-dimethyl-5-sulfo-1-(3-sulfopropyl)indolium sodium Salt (1d), (Scheme I)

Diethyl 3-acetyl-3-methylnonanedioate (IIa)

A mixture of 1.34 g (12 mmol) potassium t-butoxide and 10 g t-butanol was stirred and heated until the t-butoxide had been dissolved. The solution was cooled to about 50° C. and 1.7 g (1 1.8 mmol) of ethyl 2-methylacetoacetate (I) was added dropwise. Ethyl-6-bromohexanoate (3 g, 13.5 mmol) was then added dropwise and the reaction mixture was stirred and refluxed for 5 hours. The mixture was filtered and the solvent was removed under reduced pressure. The residue was partitioned between 1 M HCl and chloroform. The organic layer Was dried over magnesium sulfate and purified on silica gel using 1:10 ethyl acetate/hexane as the eluent to yield 2.5 g (75%) of ethyl 2-(5-carboethoxypentyl)-2-methylacetoacetate (IIa) as yellow liquid.

7-methyl-8-oxononanoic acid IIIa

The above compound IIa (8.7 mmol) was dissolved in 30 ml of methanol. A solution of 1.05 g NaOH (26.3 mmol) in 15 mL water was added. The mixture was stirred and heated at 50° C. for 20 hours. The solution was reduced to about 10 mL, acidified to pH 1 and extracted with ethyl acetate. The organic phase was collected, dried over $MgSO_4$ and evaporated to yield 1.47 g (91%) of 7-methyl-8-oxononanoic acid (IIIa) as pale orange liquid.

6-(1,2-Dimethyl-6-sulfo-1H-1-indenyl)hexanoic acid (IVa)

The nonanoic acid IIIa (7.9 mmol) was refluxed in 15 mL of acetic acid with 1.46 g of 4-hydrazinobenzenesulfonic acid (7.75 mmol) for 5 hours. The acetic acid was evaporated and the product was purified on silica gel (RP-18, $H_2O$) to yield 1.45 g (55%) of the orange solid (IVa).

Indolenine 1d

To the methanol solution of 1.1 g of Compound IVa is added 0.34 g of anhydrous sodium acetate. The mixture is stirred for five minutes. The solvent is evaporated and the resulting sodium salt is heated with 2.4 g of propane sultone at 110° C. for 1 hour to generate the final product 1d.

Synthesis of 3-(6-hydroxyhexyl)-2,3-dimethyl-5-sulfo-1-(3-sulfopropyl)indolium, sodium salt (1e)

Starting material 1e is synthesized analogously using ethyl 2-methylacetoacetate and 6-benzoyl-1-bromo-hexane in the presence of 1.2 equivalents of sodium hydride in THF according to 1d. After isolating the 3-(6-hydroxyhexyl)-2,3-dimethyl-5-sulfo-indolium, inner salt (the hydroxy group is again protected and the compound is quarternized using propanesultone. Deprotection is achieved using dilute NaOH.

1f is synthesized analogously taking into account the more polar nature of the sulfonic groups that are introduced either by reaction with 2-bromo-ethane-sulfonic acid, propane- or butanesultone. Sulfogroups can also be introduced by reaction of a 3-carboxy-alkyl-substituted compound like 1d with taurine according to Terpetschnig et al. Anal. Biochem. 217, 197-204 (1994).

Phosphate groups can be introduced in a similar way reacting ethyl 2-methylacetoacetate (I) with bromo-alkyl-phosphonates such as diethyl(3-bromopropyl)phosphonate or diethyl(2-bromoethyl)phosphonate (Aldrich) according to the above procedure (Scheme I). Conversion of the diethylphosphonates into the free acid is achieved by heating the compound in 47% HBr solution at reflux for 1.5-2 h.

Ionic and reactive groups may further be introduced into the indolenine by reacting a phenyl-hydrazine derivative with 2-acetyl-diethylmalonate or the relevant 2-acetyl-methylene-tetraethyldiphosphonate as described in Organikum, pp 480-481, Deutscher Verlag der Wissenschaften, Berlin 1990, and subsequent cleavage of the esters as described above.

Using 4-hydrazino-benzoic acid as described in Anal. Biochem. 217, 197-204 (1994) or 4-hydrazino-phenyl-acetic acid as described in Cytometry 11(3), 418-30 (1990) and reacting them in a Fisher indole synthesis with 7-methyl-8-oxononanonic acid or one of the other functionalized precursors as described above, 5-carboxy-derivatized indoles such as 1g that contain a spacer group in position 3 can be synthesized.

Other indolenine based starting materials that contain functional groups in $R_3$ and $R_4$ can be synthesized according to 1d using unsubstituted ethyl acetoacetate and 2.2 equivalents of the substituted halogen compound (ethyl-6-bromo-hexanoate, diethyl-3-bromopropyl-phosphonate, 6-benzoyl-1-bromo-hexane) and 2 equivalents of the potassium t-butoxide and are used as starting materials for squaraine dyes of this invention. $R_3$ and $R_4$ can also be a part of an aliphatic ring system as described in U.S. Patent Application Publication No. 2002/0077487. 1j is synthesized analogously to compound 1a from the commercially available 2,3,3 trimethyl-indole and bromo-hexanoic acid.

Selected precursor compounds are shown below

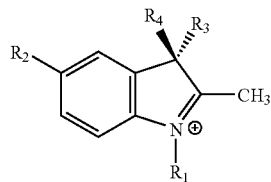

1

| 1 | $R_1$ | $R_2$ | $R_3$ (x = 2,3,4) | $R_4$ |
|---|---|---|---|---|
| a | $(CH_2)_5COOH$ | $SO_3^-$ | $CH_3$ | $CH_3$ |
| b | — | $SO_3K$ | $CH_3$ | $CH_3$ |
| c | $CH_3$ | $SO_3^-$ | $CH_3$ | $CH_3$ |
| d | $(CH_2)_3SO_3Na$ | $SO_3^-$ | $(CH_2)_5COOH$ | $CH_3$ |
| e | $(CH_2)_3SO_3Na$ | $SO_3^-$ | $(CH_2)_6OH$ | $CH_3$ |
| f | $(CH_2)_3SO_3Na$ | $SO_3^-$ | $(CH_2)_xSO_3Na$ | $CH_3$ |
| g | $(CH_2)_3SO_3^-$ | $COOH$ | $(CH_2)_5COOH$ | $CH_3$ |
| h | $(CH_2)_3SO_3Na$ | $SO_3^-$ | $CH_3$ | $CH_3$ |
| i | $(CH_2)_2PO(OH)_2$ | $SO_3^-$ | $CH_3$ | $CH_3$ |
| j | $(CH_2)_5COOH$ | $H$ | $CH_3$ | $CH_3$ |

Scheme I
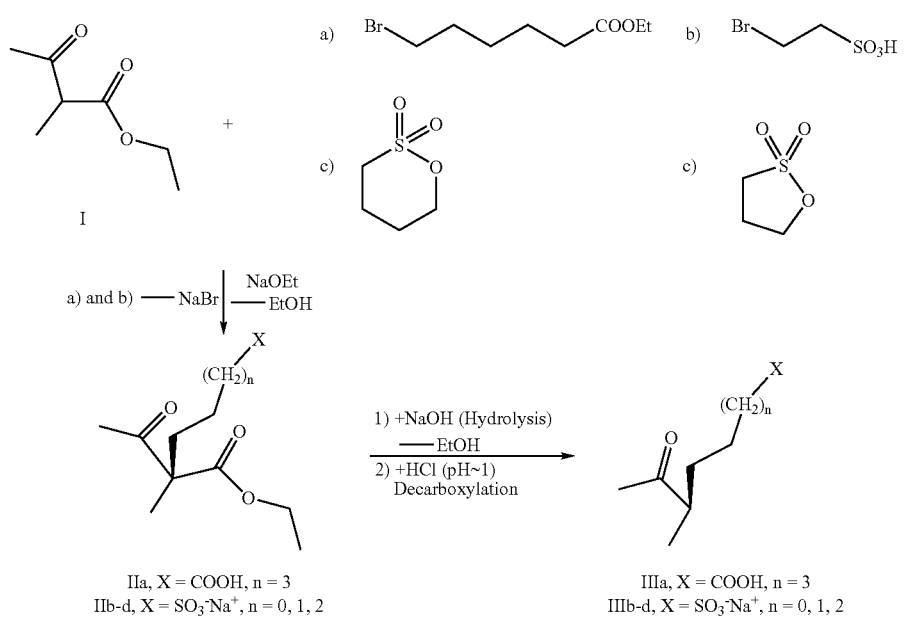
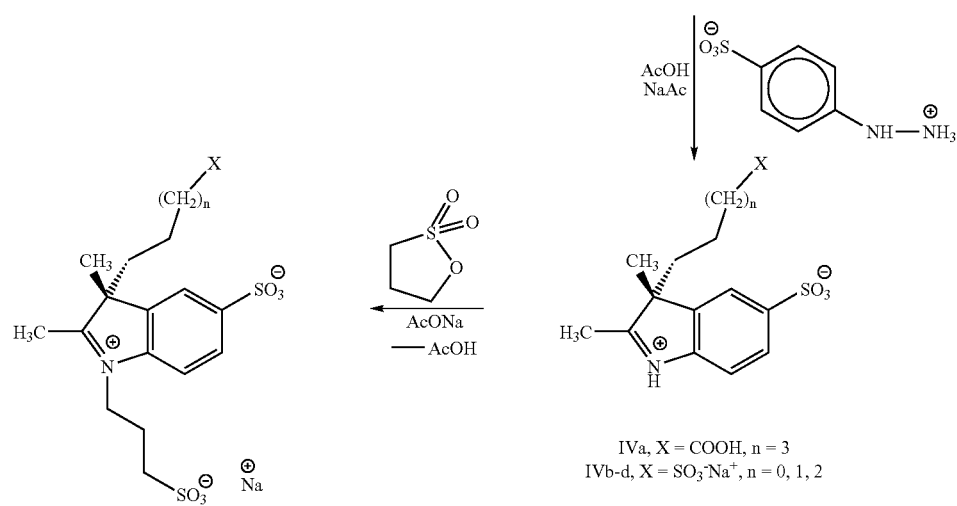
IIa, X = COOH, n = 3
IIb-d, X = SO$_3^-$Na$^+$, n = 0, 1, 2
IIIa, X = COOH, n = 3
IIIb-d, X = SO$_3^-$Na$^+$, n = 0, 1, 2
IVa, X = COOH, n = 3
IVb-d, X = SO$_3^-$Na$^+$, n = 0, 1, 2
1d, X = COOH, n = 3
1f, X = SO$_3^-$Na$^+$, n = 0, 1, 2
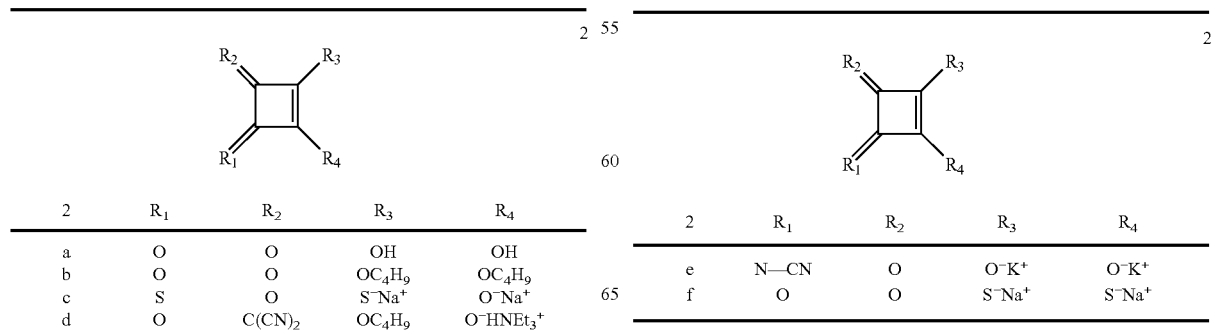
| 2 | R$_1$ | R$_2$ | R$_3$ | R$_4$ |
|---|---|---|---|---|
| a | O | O | OH | OH |
| b | O | O | OC$_4$H$_9$ | OC$_4$H$_9$ |
| c | S | O | S$^-$Na$^+$ | O$^-$Na$^+$ |
| d | O | C(CN)$_2$ | OC$_4$H$_9$ | O$^-$HNEt$_3^+$ |
-continued
| 2 | R$_1$ | R$_2$ | R$_3$ | R$_4$ |
|---|---|---|---|---|
| e | N—CN | O | O$^-$K$^+$ | O$^-$K$^+$ |
| f | O | O | S$^-$Na$^+$ | S$^-$Na$^+$ |

Example 2

Synthesis of 2,4-bis[N-(carboxypentyl)-3,3-dimethyl-5-sulfo-2-indolinylidene methyl]cyclobutenediylium-1,3-diolate NHS ester (4)

Synthesis of the di-butylester (3a)

120 mg (1.03 mmol) of squaric acid (2a) were added to 1 g (2.17 mmol) of 1-(5-carboxypentyl)-2,3,3-trimethyl-3H-5-indoliumsulfonate (1a). The resulting mixture was refluxed in 50 mL of 1-butanol:toluene (1:1, v:v) for 22 h using a Dean-Stark trap filled with 4A molecular sieve. After the mixture was cooled, the solvent was removed, and the product was purified by preparative thin-layer chromatography using RP-18 glass plates and methanol:water (2:1, v:v) as eluent to give 3a.

Yield: 90 mg (22%) of 3a; M.P.>300° C.; $R_f$: 0.47 (RP-C18, methanol/water 2/1); FAB-MS, m/e (M$^+$, dianion) for $C_{46}H_{58}N_2O_{12}S_2K_2$, calculated 895.1, found 894.8; $^1$H-NMR ($D_2O$): δ 7.7-7.1 (m, 6H), 5.7 (s, 2H), 3.7 (t, 4H, J=6.5), 2.0 (t, 4H, J=7 Hz), 1.55-0.9 (m, 24H), 1.45 (s, 12H), 0.5 (t, 6H, J=7 Hz); $\lambda_{max}$ (abs)=634 nm (PBS), $\lambda_{max}$ (em)=642 nm (PBS).

Synthesis of di-acid (3b)

1 mL of water and 20 mL of 1 M HCl were added to 50 mg (0.05 mmol) of Sq635-b-butylester (3a). The resulting mixture was heated to 100° C. for 80 min. At the end of the reaction, 5 mL of 1 M HCl were added. After the mixture was cooled, the solvent was removed, and the product was vacuum dried. The product was used without further purification Yield: 43 mg (99%); M.P.>300° C.; $R_f$: 0.75 (RP-C18, methanol:water 2:1); FAB-MS, m/e (M$^+$, dianion) for $C_{38}H_{42}N_2O_{12}S_2K_2$, calculated 782.9, found 783.0; $^1$H-NMR ($D_2O$): δ 7.8-7.3 (m, 6H), 5.9 (s, 2H), 4.2 (t, 4H, J=6.5 Hz), 2.4 (t, 4H, J=7 Hz), 1.95-1.3 (m, 12H), 1.77 (s, 12H); $\lambda_{max}$ (abs)=635 nm (PBS); $\lambda_{max}$(em)=642 nm (PBS).

Synthesis of bis-NHS-ester (4)

a) With TSTU (N,N,N',N'-tetramethyl(succinimido) uronium tetrafluoroborate)

26 μl (0.15 mmol) of diisopropylethylamine and 38 mg (0.126 mmol) of TSTU were added to a mixture of 43 mg (0.05 mmol) of Sq635-b-acid (3b) in 1 mL of DMF. After 30 min, the mixture was filtered, and the solvents were removed in vacuum. The product was dried over $P_2O_5$ and used without further purification.

Yield: 40 mg (76%); M.P.>300° C.; $R_f$: 0.82 (RP-C18, methanol:water 2:1); FAB-MS, m/e (M$^+$, dianion) for $C_{46}H_{48}N_4O_{16}S_2K_2$, calculated 977.0, found 977.1; ε=180,000 L/(mol*cm).

b) With NHS/DCC 1 mL of anhydrous DMF was added to a mixture of 20 mg (0.023 mmol) of Sq635-b-acid (3b), 14 mg (0.069 mmol) of dicyclohexylcarbodiimide (DCC), and 8 mg (0.069 mmol) of N-hydroxysuccinimide (NHS). The solution was stirred for 24 h at room temperature and then filtered. The solvent was removed in vacuum, and the product was triturated with ether and dried over $P_2O_5$.

Yield: 22 mg (91%); M.P.>300° C.; $R_f$: 0.82 (RP-C18, methanol:water 2:1); FAB-MS, m/e (M$^+$, dianion) for $C_{46}H_{48}N_4O_{16}S_2K_2$, calculated 977.0, found 977.2.

Example 3

Synthesis of 1-(5-carboxypentyl)-3,3-dimethyl-5-sulfo-3H-2-indoliumylmethylene]-2-(3,3-dimethyl-5-sulfo-2,3-dihydro-1H-2-indolylidenmethyl)-3-oxo-1-cyclobuten-1-olate (6a)

Sodium methoxide obtained from 100 mg of sodium and 1.5 ml of absolute methanol was added dropwise to a suspension of 1.0 g (1.84 mmol) of 1-(5-carboxypentyl)-2,3,3-trimethyl-3H-5-indoliumsulfonate (1a) containing 35% KBr as an impurity and 0.6 ml (2.78 mmol) of 3,4-dibutoxy-3-cy-

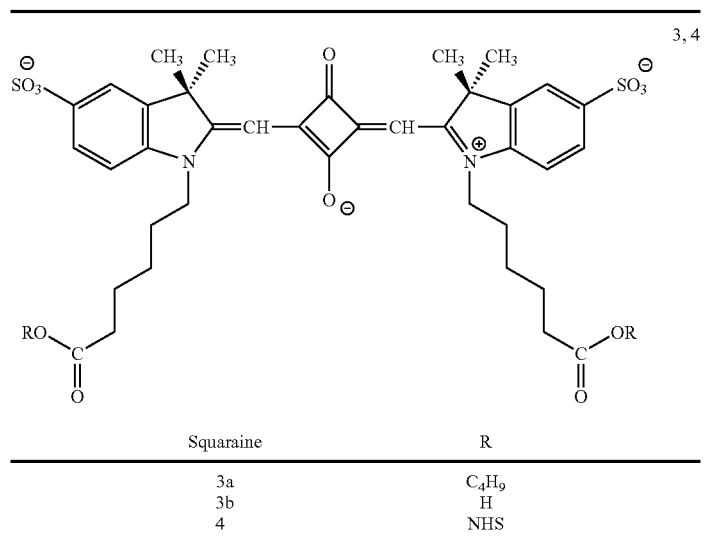

| Squaraine | R |
|---|---|
| 3a | $C_4H_9$ |
| 3b | H |
| 4 | NHS | clobutene-1,2-dione (2b) in 20 ml of absolute methanol. The solvent was removed by rotary evaporator and the residue was washed with ether and chloroform and acidified with hydrochloric acid. Acidic solution was evaporated. A mixture of obtained residue and 1.0 g (3.60 mmol) of potassium 2,3,3-trimethylindoleninium-5-sulfonate (1b) was refluxed for 8 h in a mixture of 25 ml of

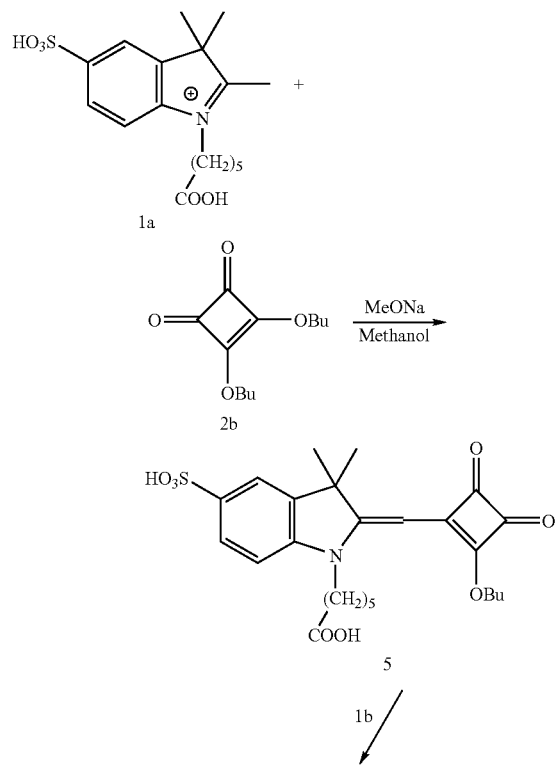

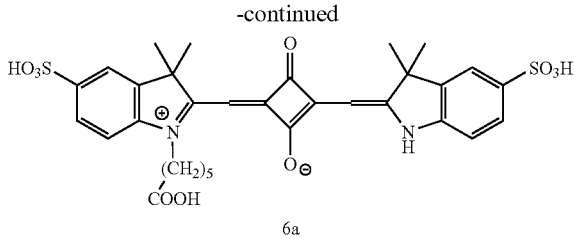

1-butanol and 15 ml of toluene. The solvent was removed under reduced pressure. The residue was twice purified by a column chromatography (Silica gel 60 RP-18, 5-20% methanol-water) to give 35 mg (3%) of the product 6a. $^1$H-NMR (200 MHz, DMSO-d$_6$), δ, ppm: 13.27 (1H, NH, s), 7.68 (1H, arom., s), 7.65 (1H, arom., s), 7.60 (1H, arom., d, 8.1 Hz), 7.55 (1H, arom., d, 8.1 Hz), 7.28 (1H, arom., d, 8.1 Hz), 7.19 (1H, arom., d, 8.1 Hz), 5.71 (1H, CH, s), 5.63 (1H, CH, s), 4.20-3.98 (2H, NCH$_2$, broad s), 2.20 (2H, CH$_2$, t, 6.8 Hz), 1.80-1.28 (6H, CH$_2$, m), 1.66 (6H, (CH$_3$)$_2$, s), 1.45 (6H, (CH$_3$)$_2$, s). λ$_{max}$(abs)=634 nm (PBS); λ$_{max}$(em)=646 nm (PBS)

Synthesis of NHS-ester (6b)

The activation of (6a) to the NHS-ester (6b) was carried out in analogy with the activation of the bis-acid (3b) procedure (b), using 1.2 equivalents of NHS and DCC.

Analysis: M.P.>300° C.; R$_f$: 0.55 (RP-C18, methanol:water 2:1); FAB-MS, m/e (M$^+$, dianion) for C$_{36}$H$_{35}$N$_3$O$_{12}$S$_2$K$_2$, calculated 766.1, found 766.4; $^1$H-NMR (D$_2$O): δ 7.85-7.5 (m, 4H), 7.15-6.9 (m, 2H), 5.55 (s,1 H), 5.35 (s, 1H), 4.45 (t, 2H, J=6.5 Hz), 2.7 (s, 4H) 2.05-2.35 (m, 2H), 1.5-1.2 (m, 6H), 1.25 (t, 12H).

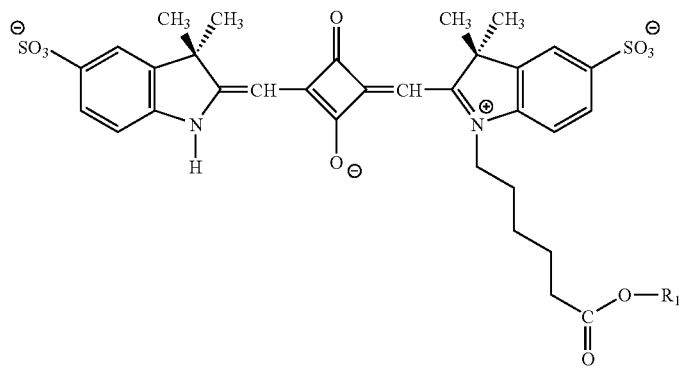

| Squaraine | R$_1$ |
|---|---|
| 6a | H |
| 6b | NHS |

Example 4

Synthesis of 2-[3,3-dimethyl-2-1(H)indolinylidenemethyl]4-[1-ethyl-benzoselen azolinylidene-methyl]cyclobutenediylium-1,3-dioxolate (8) and dithiolate (9)

1[-3'-Ethyl-2(3H)benzoselenazolylidene-2-methyl]3-ethoxycyclobuten-3,4-dione (7a)

15 mmol of N-ethyl-2-methylbenzoselenazolium iodide were added to a stirred hot solution of 10 mmol diethylsquarate and 2 mL triethylamine in 15 mL of ethanol. The solution was kept at 70-80° C. for 5 min, and then cooled to room temperature. The resulting yellow-to-red colored precipitate was isolated, washed with ethylether, and dried. The product was purified by column chromatography on silica gel using $CHCl_3$:EtOAc (9:1, v:v) as eluent.

Yield: 58%; M.P.=278-80° C.; $^1$H-NMR ($D_6$-DMSO): δ 1.40 (t, 3H), 1.52 (t, 3H), 4.07 (q, 2H), 4.84 (q, 2H), 5.69 (s, 1H), 7.05 (d, 1H), 7.13 (t, 1H), 7.35 (t, 1H), 7.55 (d, 1H).

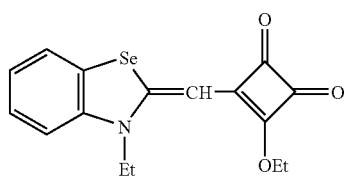

7a

2-Hydroxy-1-[3'-ethyl-2(3H)benzoselenazolylidene-2'-methyl]cyclobuten-3,4-dione (7b)

5 mmol of (7a) were suspended in 20 mL of boiling ethanol, and dissolved on addition of 0.6 mL of 40% NaOH. The solution was kept at boiling for another 5 min and then cooled to room temperature. After addition of 6-7 mL of 2 M HCl, the ethanol solution was concentrated, and the resulting precipitate 7b was collected and used without further purification.

Yield: 95%; M.P.=252-254° C.; $^1$H-NMR($D_6$-DMSO): δ 1.24 (t, 3H), 4.07 (q, 2H), 4.1 (q, 2H), 6.08 (s, 1H), 7.09 (t, 1H), 7.32 (m, 2H), 7.81 (d, 1H).

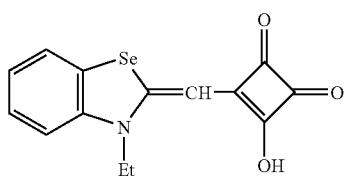

7b

Unsymmetrical Dioxo-squaraine (8)

1 mmol of the squaric acid derivative (7b) and 1 mmol of 2,3,3-trimethylindolenine (from Aldrich) were heated under reflux in a mixture of 20 mL toluene and 20 mL 1-butanol. Water was removed azeotropically using a Dean-Stark trap. After 16 h, the reaction was cooled to room temperature, and the solvents were removed under vacuum. The residue was treated with ether, and the product was isolated by filtration. Further purification was achieved using column chromatography with chloroform-2-propanol mixtures as eluent.

Yield: 80% of (8); $^1$H-NMR(CDCl$_3$): δ 1.5 (s, 9H), 4.25 (m, 2H), 5.45 (s, 2H), 7.65-7.15 (m, 8H), 12.2 (s, 1H). $\lambda_{max}$(abs)=666 nm (CHCl$_3$); $\lambda_{max}$(em)=692 nm (CHCl$_3$).

Unsymmetrical Thiosquaraine (9)

20 mg of 8 and 30 mg of $P_2S_5$ were refluxed for 4 h in 2 mL of pyridine under stirring. The solvent was removed under reduced pressure, and the residue was treated with chloroform. Chloroform was removed under reduced pressure, and the product was purified using preparative TLC, again using chloroform as the solvent system.

Analysis: $\lambda_{max}$(abs)=687 nm (CHCl$_3$); $\lambda_{max}$(em)=724 nm (CHCl$_3$).

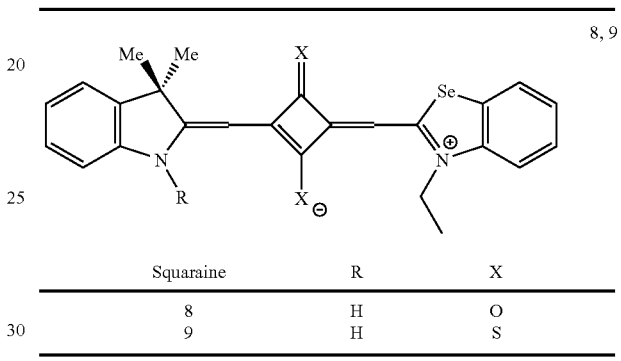

8, 9

| Squaraine | R | X |
|---|---|---|
| 8 | H | O |
| 9 | H | S |

Example 5

Synthesis of 4-[1-(5-carboxypentyl)-3,3-dimethyl-5-sulfo-3H-2-indoliumylmethylene]-3-dicyanomethylene-2-(3,3-dimethyl-4,7-disulfo-2,3-dihydro-1H-2-indolylidenmethyl)-1-cyclobuten-1-olate (10)

Dipotassium 2,3,3-trimethyl-3H-4,7-indoledisulfonate (1k)

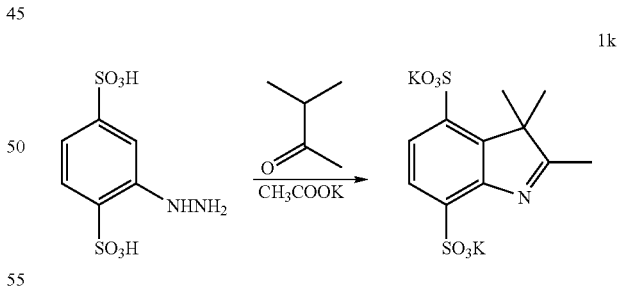

1k

To a three-necked flask equipped with mechanical stirrer and a reflux condenser were added 50 ml of acetic acid, 15 ml (140 mmol) of 3-methyl-2-butanone, 16.2 g (60 mmol) of 2-hydrazino-1,4-benzenedisulfonic acid and 13 g (133 mmol) of potassium acetate. The mixture was heated to reflux for 8 h and then cooled to room temperature. The brownish precipitate was filtered off and washed with acetic acid and acetonitrile. Yield: 13.8 g (58%) of the raw product (1k). $^1$H-NMR (200 MHz, DMSO-d$_6$), δ, ppm: 7.67 (1H, arom., d, 8.1 Hz), 7.59 (1H, arom., d, 8.2 Hz), 2.44 (3H, CH$_3$, s), 1.57 (6H, (CH$_3$)$_2$, s).

Triethylammonium 3-oxo-2-[1-(5-carboxypentyl)-3,3-dimethyl-2,3-dihydro-1H-2-indoliden methyl]-4-oxo-1-cyclobuten-1-olate (11)

1.2 ml (8.57 mmol) of TEA was added dropwise to a mixture of 1.4 g (3.95 mmol) of 1-(3-carboxypentyl)-2,3,3-trimethyl-3H-indolium bromide (1j), 0.9 ml (4.16 mmol) of 3,4-dibutoxy-3-cyclobutene-1,2-dione (2b) in 8.5 ml of ethanol and stirred overnight at room temperature. Afterwards the solvent was removed under reduced pressure. The raw product was column purified (Silica gel 60, 0-1% methanol-chloroform (v/v)) to give (1.2 g, 71.4%) 6-[2-(2-butoxy-3,4-dioxo-1-cyclobutenylmethylene)-3,3-dimethyl-2,3-dihydro-1H-1-indolyl]hexanoic acid (11).

Triethylammonium 3-dicyanomethylene-2-[1-(5-carboxypentyl)-3,3-dimethyl-2,3-dihydro-1H-2-indolylidenmethyl]-4-oxo-1-cyclobuten-1-olate (12)

A mixture of 1.2 g (2.82 mmol) of 11, 190 mg (2.87 mmol) of malononitrile and 0.4 ml (2.85 mmol) of TEA in 15 ml of ethanol was stirred at room temperature for 2.5 h. Then solvent was removed by a rotary evaporator. Product 12 was used in next synthesis without further purification.

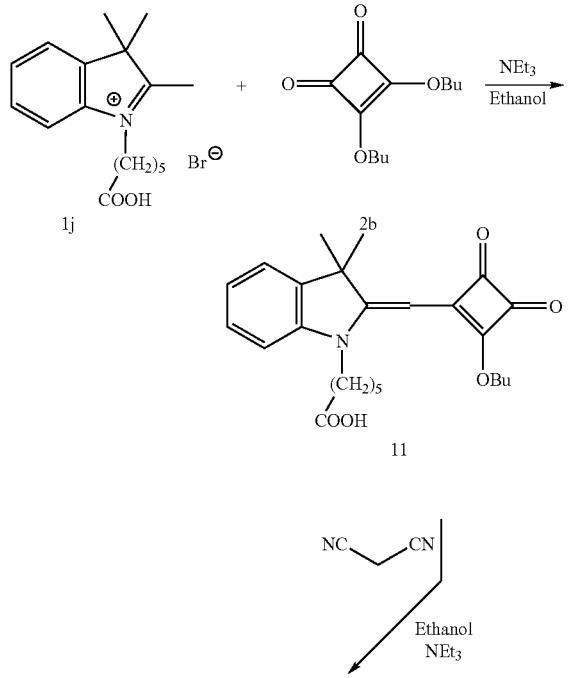

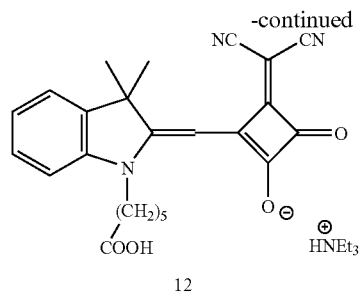

4-[1-(5-carboxypentyl)-3,3-dimethyl-5-sulfo-3H-2-indoliumylmethylene]-3-dicyanomethylene-2-(3,3-dimethyl-4,7-disulfo-2,3-dihydro-1H-2-indoliden-methyl)-1-cyclobuten-1-olate (10)

A mixture of 290 mg (0.56 mmol) of triethylammonium 3-dicyanomethylene-2-[1-(5-carboxypentyl)-3,3-dimethyl-2,3-dihydro-1H-2-indolylidenmethyl]-4-oxo-1-cyclobuten-1-olate (12) and 350 mg of dipotassium 2,3,3-trimethyl-3H-4,7-indoledisulfonate (1k) was refluxed for 22 h in a mixture of 20 ml of 1-butanol and 1.5 ml of water. The solvent 10 was then removed under reduced pressure and the residue was purified by column chromatography (Silica gel 60 RP-18, methanol-water, 3:2 v/v) to give 30 mg of product (13). 23 mg of 13 was dissolved in 3 ml of water and then 750 μl of 1 M KOH was added. This mixture was stirred overnight, acidified with 1 M hydrochloric acid to pH=2. Water was evaporated and the residue was column purified (Silica gel 60 RP-18, methanol-water, 3:7 v/v) to give product (10). Yield: 10 mg. $^1$H-NMR (200 MHz, DMSO-$d_6$), δ, ppm: 12.32 (1H, NH, s), 7.60 (1H, arom., d, 7.0 Hz), 7.56 (1H, arom., d, 8.2 Hz), 7.48 (1H, arom., d, 8.2 Hz), 7.45-7.36 (2H, arom., m), 7.32-7.19 (1H, arom., m), 6.24 (1H, CH, s), 5.77 (1H, CH, s), 4.13-3.91 (2H, NCH$_2$, broad s), 3.08 (6H, q, 7.3, 14.4 Hz, N(CH$_2$CH$_3$)$_3$), 2.19 (2H, CH$_2$, t, 6.8 Hz), 1.83-1.28 (6H, CH$_2$, m), 1.69 (12H, (CH$_3$)$_2$, s), 1.17 (9H, t, 7.2 Hz, N(CH$_2$CH$_3$)$_3$). $\lambda_{max}$ (abs): 655 nm (water), $\lambda_{max}$ (em): 678 nm (water). The NHS ester of 10 is synthesized analoguously to compound 6b.

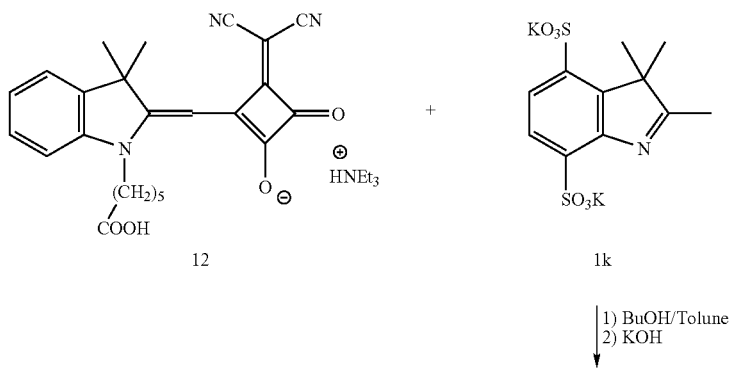

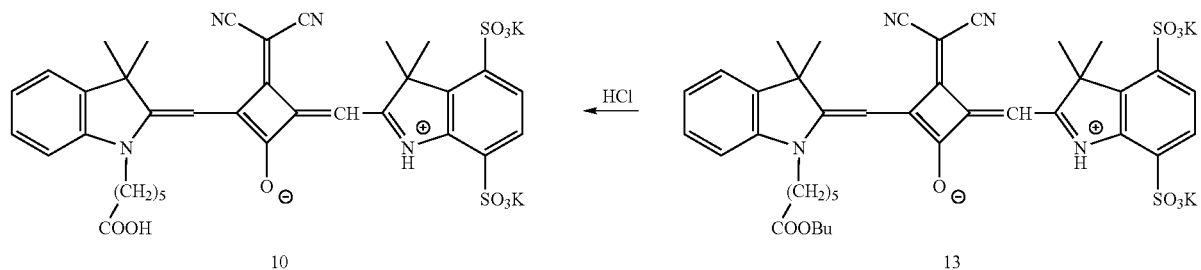

Example 6

2-(3,3-dimethyl-5-sulfo-2,3-dihydro-1H-2-indolylidenmethyl)-4-(3,3-dimethyl-5-sulfo-3H-2-indolylmethylene)-3-oxo-1-cyclobuten-1-olate (14)

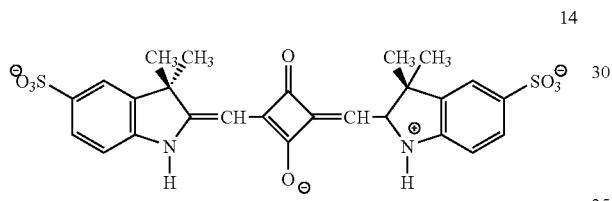

A mixture of 150 mg (0.54 mmol) potassium 2,3,3-trimethylindoleninium-5-sulfonate (1b) and 30 mg (0.26 mmol) of 3,4-dihydroxy-3-cyclobutene-1,2-dione (2a) was refluxed in 20 ml of a 1-butanol-toluene mixture (1:1 v/v) for 15 h. The solvent was removed under reduced pressure. The residue was purified by column chromatography (Silica gel 60 RP-18, 0-20% methanol-water) to give 42 g (29%) of the product 14. $^1$H-NMR (200 MHz, DMSO-d$_6$), δ, ppm: 12.78 (2H, NH, broad s), 7.65 (2H, arom., s), 7.55 (2H, arom., d, 8.0 Hz), 7.16 (2H, arom., d, 8.1 Hz), 5.59 (2H, CH, s), 1.45 (12H, (CH$_3$)$_2$, s).

Example 7

Synthesis of 2-[3-(5-carboxypentyl)-3-methyl-5-sulfo-2,3-dihydro-1H-2-indolyliden methyl]-4-{(E)-1-[3-(5-carboxypentyl)-3-methyl-5-sulfo-3H-2-indoliumyl]methylidene}-3-oxo-1-cyclobuten-1-olate (15)

A mixture of 60 mg (0.5 mmol) of squaric acid 2a, 500 mg (1.47 mmol) of 3-(5-carboxypentyl)-2,3-dimethyl-5-indoliumsulfonic acid IVa, 10 ml of butanol and 10 ml of toluene was refluxed for 18 hours. The solvent was evaporated, the residue was dissolved in 20 ml of the 0.25 M HCl and refluxed for 3 hours. The solvent was removed under reduced pressure and product was purified on silica gel (RP-18, H$_2$O-MeOH) to yield 50 mg of the dark-blue solid 15. $^1$H-NMR (200 MHz, DMSO-d$_6$), δ, ppm: 12.80 (2H, s), 7.60 (2H, arom., s), 7.56 (2H, arom., d, 8.3 Hz), 7.16 (2H, arom., d, 8.2 Hz), 5.55 (2H, CH, s), 2.08 (4H, CH$_2$, t, 6.8 Hz), 2.04-1.75 (4H, CH2, m), 1.42 (6H, CH3, s), 1.42-1.01 (8H, CH2, m), 1.00-0.74 (2H, CH2, m), 0.73-0.47 (2H, CH2, m). λ$_{max}$(abs)=640 nm (water); λ$_{max}$(em)=657 nm (PBS).

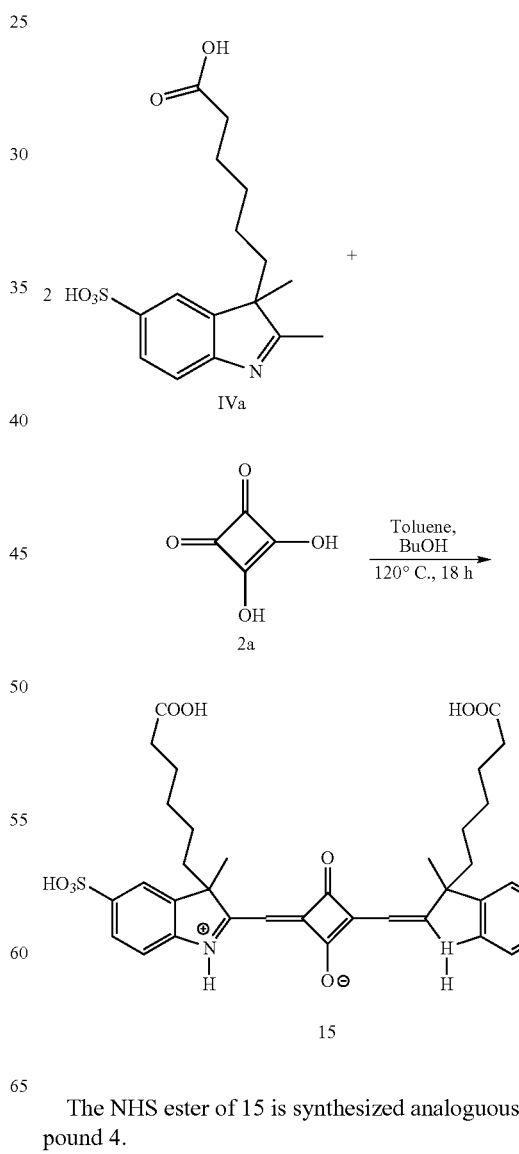

The NHS ester of 15 is synthesized analoguously to compound 4.

Example 8

Synthesis of 2-[3-(5-carboxypentyl)-3-methyl-5-sulfo-2,3-dihydro-1H-2-indolylmethyl]-4-[3-(5-carboxypentyl)-3-methyl-5-sulfo-3H-2-indoliumylmethyl]-3-dicyanomethylene-1-cyclobuten-1-olate (16)

Triethylammonium 2-butoxy-3-dicyanomethylene-4-oxo-1-cyclobuten-1-olate (2d)

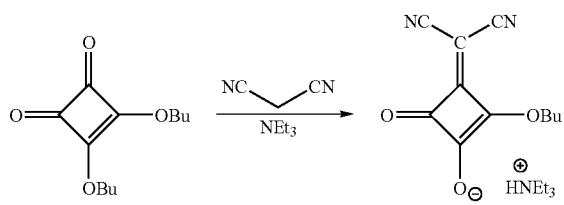

2.16 ml (10 mmol) of 3,4-dibutoxy-3-cyclobutene-1,2-dione (2b) was dissolved in 20 ml of anhydrous benzene, and 660 mg (10 mmol) of malonodinitrile was added under stirring. Then, 1.65 ml (12 mmol) of triethylamine was added dropwise for 5 min followed by 10 ml of anhydrous benzene. The obtained emulsion is stirred for 30 min at room temperature. The solvent is removed using a rotary evaporator. The yellow oiled residue is treated three times with ether to give crude product 2d (1.8 g, 56%), $^1$H-NMR (200 MHz, DMSO-$d_6$), δ, ppm: 10.15-9.55 (1H, broad S, NH$^+$), 4.59 (2H, t, 6.7 Hz, OCH$_2$), 3.07 (6H, q, 7.4, 14.5 Hz, N(CH$_2$CH$_3$)$_3$), 1.77-1.58 (2H, m, CH$_2$), 1.48-1.26 (2H, m, CH$_2$), 1.18 (9H, t, 7.3 Hz, N(CH$_2$CH$_3$)$_3$), 0.90 (3H, t, 7.4 Hz, CH$_3$).

2-[3-(5-carboxypentyl)-3-methyl-5-sulfo-2,3-dihydro-1H-2-indolylmethyl]-4-[3-(5-carboxypentyl)-3-methyl-5-sulfo-3H-2-indoliumylmethyl]-3-dicyanomethylene-1-cyclobuten-1-olate (16)

A mixture of 0.3 g (1 mmol) of 2d, 0.8 g (2.5 mmol) of 3-(5-carboxypentyl)-2,3-dimethyl-5-indoliumsulfonic acid IVa, 20 ml of butanol and 20 ml of toluene was refluxed for 34 hours. The solvent was evaporated, the residue was dissolved in 20 ml of the 0.25 M HCl and refluxed for 4 hours. The solvent was removed under reduced pressure and product was purified on silica gel (RP-18, H$_2$O-MeOH) to yield 355 mg of the dark-green solid 16. $\lambda_{max}$(abs)=674 nm (water), $\lambda_{max}$(em)=697 nm (water).

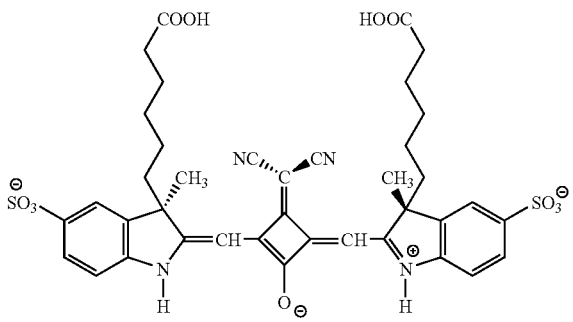

The NHS ester of 16 is synthesized according to Example 4.

Example 9

Synthesis of 2,4-Bis[N-(5-butoxycarbonylpentyl)-3,3-dimethyl-5-sulfo-2-indolinylidenemethyl]cyclobutenediylium-3-dicyanomethylene-1-olate (17)

472 mg of 1-(5-carboxypentyl)-2,3,3-trimethyl-3H-5-indoliumsulfonate (1a) and 137 mg of triethylammonium 2-butoxy-3-dicyanomethylene-4-oxo-1-cyclobuten-1-olate (2d) were refluxed in 25 mL of butanol:toluene (1:1, v:v) for 4 h using a Dean-Stark trap. After the mixture was cooled to room temperature, the solvents were removed in vacuum, and the raw product was triturated with ether and dried. The raw product was

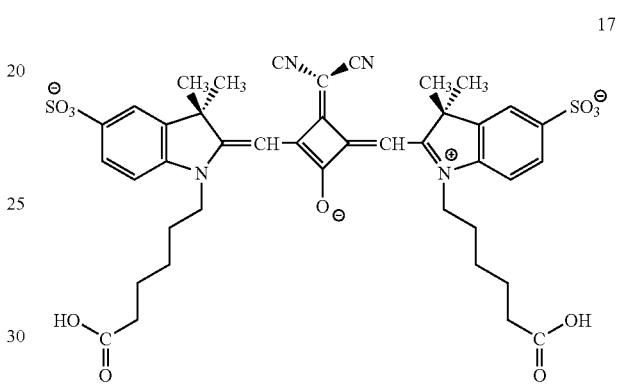

purified by preparative thin-layer chromatography on RP-18 glass plates using a methanol/water mixture (2/1, v:v) as eluent. The blue-green band with an $R_f$ of 0.55 was collected.

Yield: 32%; FAB-MS m/e calculated for $C_{41}H_{44}N_4O_{11}S_2K_2$ (M$^{2-}$) 832.9, found 633.2. IR (KBr): 2100 cm$^{-1}$ (CN). $^1$H-NMR (D$_2$O): δ 8.00 (2H, s), 7.90 (2H, d), 7.75 (2H, d), —CH= is exchanged, 4.45 (4H, t), 2.10(4H, t), 1.85 (4H, m), 1.55 (4H, m), 1.45 (12H, s), 1.35 (4H, m); $\lambda_{max}$ abs)=667 nm (PBS), $\lambda_{max}$(em)=685 nm (PBS), (Q.Y.=7%); ε=188.000 L/mol*cm (H$_2$O).

Example 10

3-dicyanomethylene-2-(3,3-dimethyl-5-sulfo-2,3-dihydro-1H-2-indolylidenmethyl)-4-(3,3-dimethyl-5-sulfo-3H-2-indolylmethylene)-1-cyclobuten-1-olate (18)

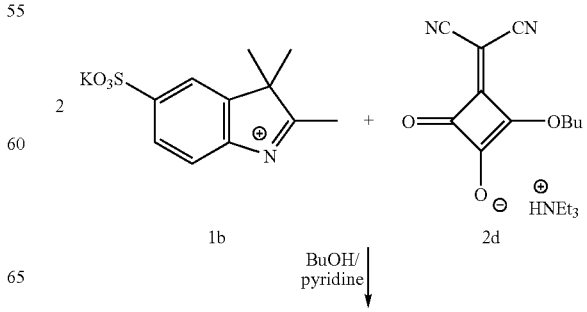

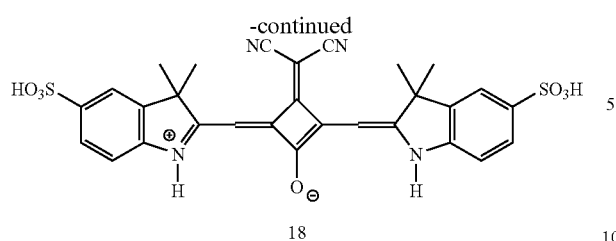

18

A mixture of 100 mg (0.36 mmol) of potassium 2,3,3-trimethylindoleninium-5-sulfonate (1b) and 50 mg (0.16 mmol) of triethylammonium 2-butoxy-3-dicyanomethylene-4-oxo-1-cyclobuten-1-olate (2d) was refluxed in 20 ml of a 1-butanol-pyridine mixture (1:1 v/v) for 13.5 h. The solvent was removed under reduced pressure. The residue was washed with chloroform and purified by column chromatography (Silica gel 60 RP-18, 0-30% methanol-water) to give 25 mg (26%) of product 18. $^1$H-NMR (200 MHz, DMSO-$d_6$), δ, ppm: 12.10 (2H, NH, s), 7.73 (2H, arom., s), 7.62 (2H, arom., d, 8.1 Hz), 7.32 (2H, arom., d, 8.1 Hz), 5.68 (2H, CH, s), 1.44 (12H, (CH$_3$)$_2$, s).

Example 11

Synthesis of 1-(5-carboxypentyl)-2-{3-[1-(5-carboxypentyl)-1-methyl-6,8-disulfonato-2,3-dihydro-1H-benzo[e]indol-2-ylidenmethyl]-2-olato-4-oxo-2-cyclobutenylidenmethyl}-1-methyl-1H-benzo[e]indolium-6,8-disulfonate (20).

The synthesis of the disulfo-naphthyl-hydranzine is described in Bioconjugate Chem., Vol 7 (3), 356-362 (1996) and the synthesis of compound 19 is described in U.S. Patent Application Publication No. 2002/0077487.

A mixture of 60 mg (0.5 mmol) of squaric acid 2a, 702 mg (1.25 mmol) of 19, 15 ml of butanol and 15 ml of toluene was refluxed for 18 hours. The solvent was evaporated, the residue was dissolved in 20 ml of the 0.25 M HCl and refluxed for 3 hours. The solvent was removed under reduced pressure and product was purified on silica gel (RP-18, H$_2$O-MeOH) to yield 40 mg product 20. The NHS ester is synthesized analoguously to compound 4.

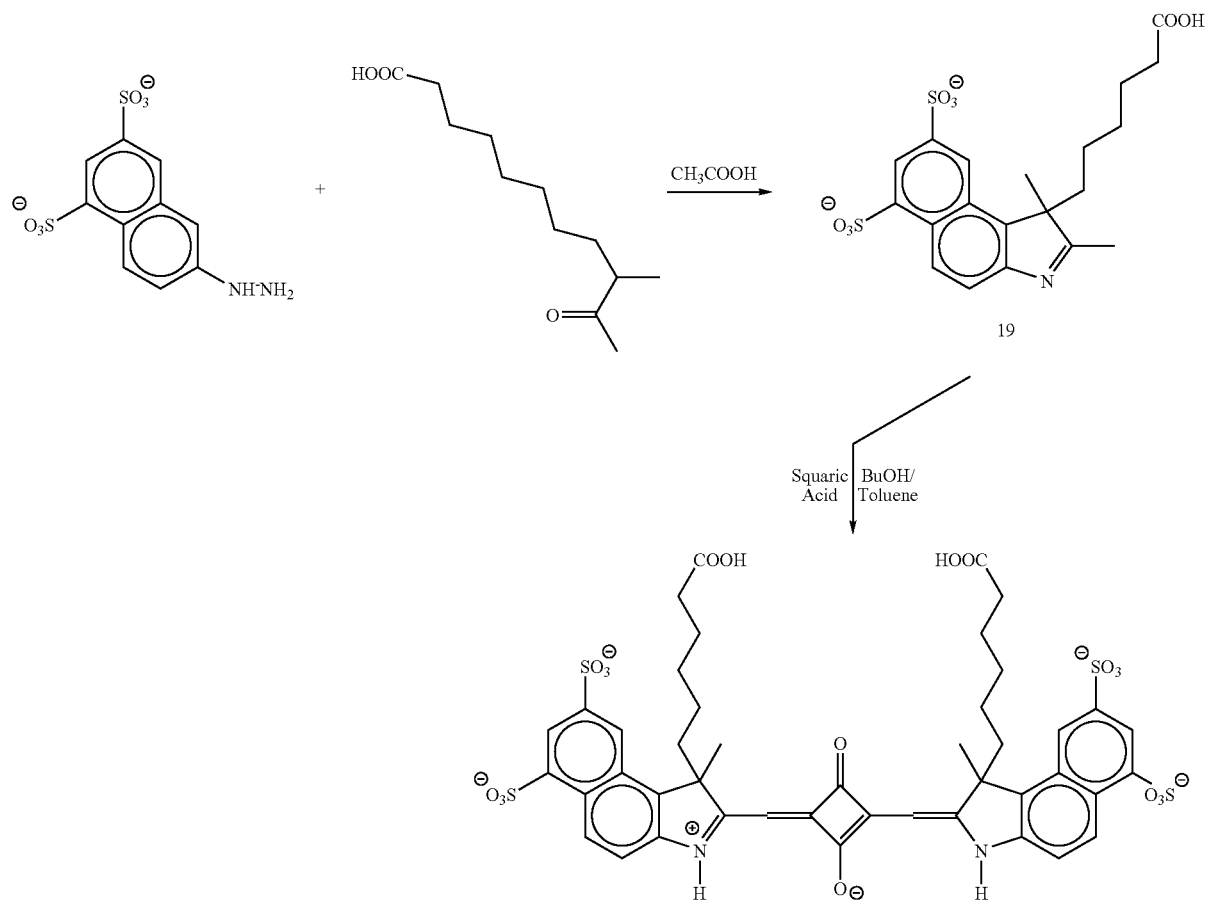

Monoreactive derivatives of bisfunctional squaraines dyes such as 15, 16 or 20 can be obtained by derivatizing one carboxyl group with taurine (2-amio-ethanesulfonic acid) and subsequent activation of the carboxy group to the mono-NHS ester.

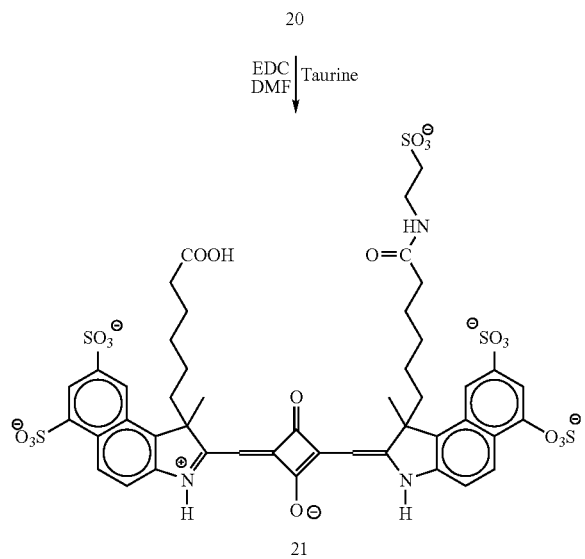

Example 12

Synthesis of 2-[1-(5-Carboxypentyl)-3,3-dimethyl-5-sulfo-2,3-dihydro-1H-2-indolylidenmethyl]-4-[1-(5-carboxypentyl)-3,3-dimethyl-5-sulfo-3H-2-indoliumylmethylene]-3-oxo-1-cyclobutene-1-thiolate (22)

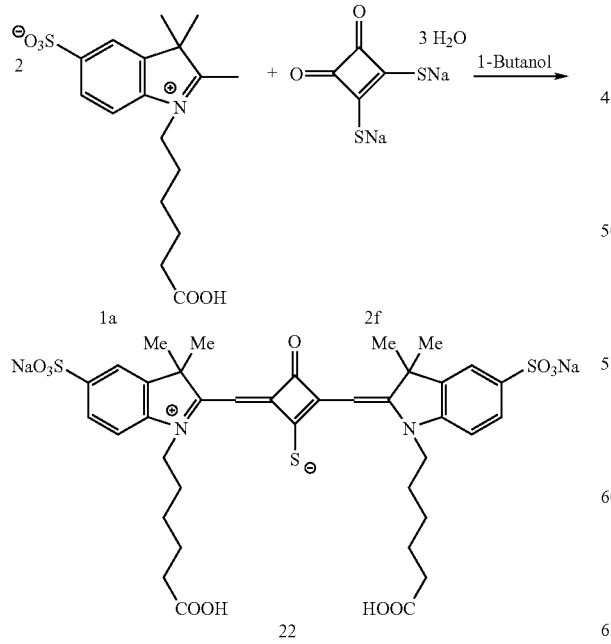

A mixture of 1.45 g (2.5 mmol) of 1-(5-carboxypentyl)-2,3,3-trimethyl-3H-5-indoliumsulfonate (1a) and 0.24 g (1.0 mmol) disodium-3,4-dioxo-1-cyclobutene-1,2-dithiolate trihydrate (2f) in 40 ml of 1-butanol is heated under reflux for 6 h. The solvent is removed under reduced pressure and the residue is purified twice by column chromatography (LiChroprep RP-18, 5-20% methanol-water) to give product 22. $^1$H-NMR (200 MHz, DMSO-d$_6$), δ, ppm: 7.71 (2H, arom., s), 7.64 (2H, arom., d, 8.3 Hz), 7.30 (2H, arom., d, 8.3 Hz), 6.21 (2H, CH, s), 4.23-4.04 (4H, NCH$_2$, broad s), 2.21 (4H, t, 7.0 Hz), 1.71 (12H, (CH$_3$)$_2$, s), 1.85-1.32 (12H, m). Element analysis: S (found)=12.00%, S (calcd)=11.39%.

UV: $\lambda_{max}$ (abs) 638 nm, $\epsilon$=215,000 (water); $\lambda_{max}$ (em) 654 nm (water).

Example 13

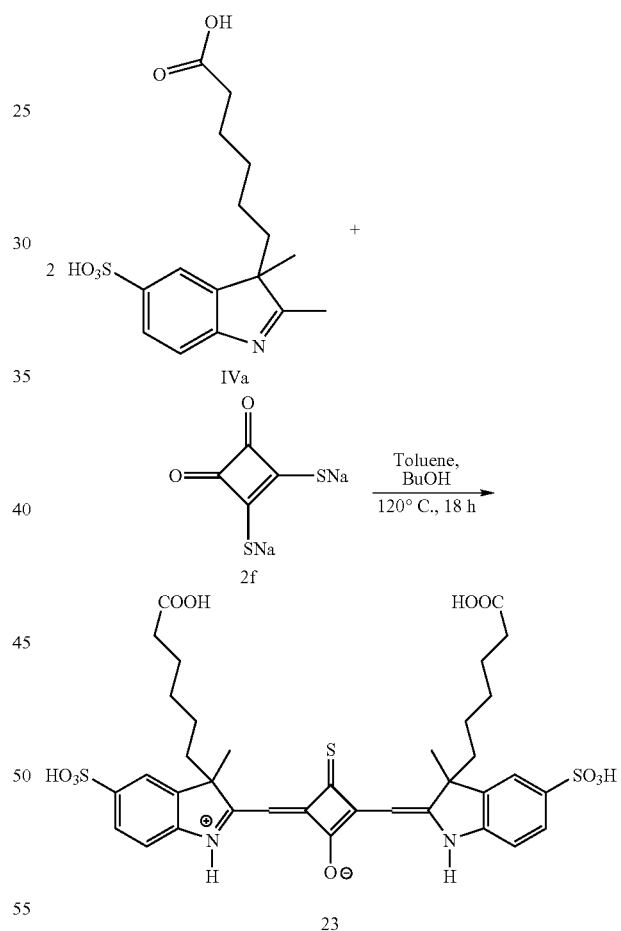

A mixture of 120 mg (0.5 mmol) of disodium-3,4-dioxo-1-cyclobutene-1,2-dithiolate trihydrate 2f, 500 mg (1.47 mmol) of 3-(5-carboxypentyl)-2,3-dimethyl-5-indoliumsulfonic acid IVa, 10 ml of butanol and 10 ml of toluene was refluxed for 18 hours. The solvent was evaporated and the residue dissolved in 20 ml of the 0.25 M HCl and refluxed for 3 hours. The solvent was removed under reduced pressure and the product was purified on silica gel (RP-18, H$_2$O-MeOH) to yield dye 23.

Example 14

General Protein Labelling Procedures and Determination of Dye-to-Protein Ratios Protein labelling reactions were carried out using a 50 mM bicarbonate buffer (pH 9.1). A stock solution of 1 mg of dye in 100 μL of anhydrous DMF was prepared. 10 mg of protein were dissolved in 1 mL of 50 mM bicarbonate buffer (pH 9.0). Dye from the stock solution was added, and the mixture was stirred for 2-4 h at room temperature.

Unconjugated dye was separated from labelled proteins using gel permeation chromatography with SEPHADEX G50 (0.5 cm×20 cm column) and a 22 mM phosphate buffer solution (pH 7.3) as the eluent. The first colored band contained the dye-protein conjugate. A later blue (green) band with a much higher retention time contained the separated free dye. A series of labelling reactions as described above were set up to obtain different dye-to-protein ratios. Compared to the free forms, the protein-bound forms of the dyes show distinct changes in their spectral properties.

Protein concentration was determined using the BCA Protein Assay Reagent Kit from Pierce (Rockford, Ill.). The dye-to-protein ratio (D/P) gives the number of dye molecules covalently bound to the protein.

Covalent Attachment of the NHS-ester of 15 to Polyclonal Anti-HSA Antibody

385 μL (5.2 mg/mL) of anti-HSA were added to 600 μL bicarbonate buffer (0.1 M, pH 9.0). 1 mg of NHS-ester of 15 was dissolved in 50 μL of DMF and slowly added to the above-prepared protein solution with stirring. After 20 h of stirring, the protein-conjugate was separated from the free dye using Sephadex G50 and a phosphate buffer (22 mM, pH 7.2). The first blue band that was isolated contained the labeled conjugate.

Conjugation of 6b to HSA 0.5 mg of (6b) in 50 μL of DMF were slowly added to a stirred solution of 5 mg of HSA in 750 μL of bicarbonate buffer (0.1 M, pH 9.0). The mixture was stirred for another 6 h at room temperature. The mixture was dialyzed against a phosphate buffer (22 mM, pH 7.2) using a dialysis membrane (1500 FT, Union Carbid) with a cutoff of 10.000.

Analysis: $\lambda_{max}$(abs)=635 nm (PBS); $\lambda_{max}$ (em)=660 nm (PBS).

Similar reactions were performed using alternative reporter compounds having reactive NHS ester functional groups.

Fluorescence Decay Times of Various Dyes:

The following table lists the fluorescence decay times of representative dyes. The experimental conditions included (1) excitation with a "spark lamp" using a 300-380 nm band pass filter, (2) emission was observed at 675 nm (4 mm slit) using grating monochrometer (1200 lines/mm), and (3) a temperature of 20° C.

| Sample | Decay Time [ns] | Amplitude | Fractional Intensity | Chi Square |
|---|---|---|---|---|
| 3b | 0.2 | 1 | 1 | 7.9 |
| 15 | 2.0 | 1 | 1 | 4.9 |
| 16 | 1.9 | 1 | 1 | 5.6 |
| Cy5 | 1.1 | 1 | 1 | 2.1 |

Spectral Properties and of Representative Squaraine Dyes:

The following table summarizes absorption (excitation) and emission spectral data for representative dyes in absence and presence of BSA:

| Squaraine | $\lambda_{max}$(abs) [nm] | $\lambda_{max}$ (em) [nm] | $\epsilon$ [L · Mol$^{-1}$ × cm$^{-1}$] |
|---|---|---|---|
| 3b | 635 | 642 | 180.000 |
| 3b (BSA) | 642 | 653 | — |
| 6a | 634 | 646 | 120.000 |
| 6a (BSA) | 635 | 660 | — |
| 10 | 655 | 678 | 150.000 |
| 10 (BSA) | 682 | 797 | — |
| 15 | 640 | 657 | 190.000 |
| 15 (BSA) | 655 | 670 | — |

Example 15

Description of Applications of the Invention

The reporter compounds disclosed above exhibit utility for a variety of useful methods for various assay formats.

The assay may be a competitive assay that includes a recognition moiety, a binding partner, and an analyte. Binding partners and analytes may be selected from the group consisting of biomolecules, drugs, and polymers, among others. In some competitive assay formats, one or more components are labeled with photoluminescent compounds in accordance with the invention. For example, the binding partner may be labeled with such a photoluminescent compound, and the displacement of the compound from an immobilized recognition moiety may be detected by the appearance of fluorescence in a liquid phase of the assay. In other competitive assay formats, an immobilized enzyme may be used to form a complex with the fluorophore-conjugated substrate.

The binding of antagonists to a receptor can be assayed by a competitive binding method in so-called ligand/receptor assays. In such assays, a labeled antagonist competes with an unlabelled ligand for the receptor binding site. One of the binding partners can be, but not necessarily has to be, immobilized. Such assays may also be performed in microplates. Immobilization can be achieved via covalent attachment to the well wall or to the surface of beads.

Other preferred assay formats are immunological assays. There are several such assay formats, including competitive binding assays, in which labeled and unlabeled antigens compete for the binding sites on the surface of an antibody (binding material). Typically, there are incubation times required to provide sufficient time for equilibration. Such assays can be performed in a heterogeneous or homogeneous fashion.

Sandwich assays may use secondary antibodies and excess binding material may be removed from the analyte by a washing step.

Other types of reactions include binding between avidin and biotin, protein A and immunoglobulins, lectins and sugars (e.g., concanavalin A and glucose).

The reporter compounds described here also may be used to sequence nucleic acids and peptides. For example, fluorescently-labeled oligonucleotides may be used to trace DNA fragments. Other applications of labeled DNA primers include fluorescence in-situ hybridization methods (FISH) and for single nucleotide polymorphism (SNIPS) applications, among others.

Multicolor labeling experiments may permit different biochemical parameters to be monitored simultaneously. For this purpose, two or more reporter compounds are introduced into the biological system to report on different biochemical functions. The technique can be applied to fluorescence in-situ hybridization (FISH), DNA sequencing, fluorescence microscopy, and flow cytometry. One way to achieve multicolor analysis is to label biomolecules such as nucleotides, proteins or DNA primers with different luminescent reporters having distinct luminescence properties. Luminophores with narrow emission bandwidths are preferred for multicolor labeling, because they have only a small overlap with the other dyes and hence increase the number of dyes possible in a multicolor experiment. Importantly, the emission maxima have to be well separated from each other to allow sufficient resolution of the signal. A suitable multicolor triplet of fluorophores would include Cy3, TRITC, and a photoluminescent compound as described herein, among others.

The simultaneous use of FISH (fluorescence in-situ hybridization) probes in combination with different fluorophores is useful for the detection of chromosomal translocations, for gene mapping on chromosomes, and for tumor diagnosis, to name only a few applications. One way to achieve simultaneous detection of multiple sequences is to use combinatorial labeling. Up to seven different DNA targets can be simultaneously visualized by using a combination of haptenated DNA probes (e.g. biotin, digoxigenin or dinitrophenol) with three sets of distinguishable fluorophores showing emission in the green (fluorescein), red (TEXAS RED), and blue (7-amino-4-methyl-coumarin-3-acidic acid or CASCADE BLUE) (Ried, T. et al., Proc. Natl. Acad. Aci. USA 89:1388-1392, (1992). Three labeled DNA probes can be visualized by the distinct spectra of the three fluorescent markers, while four others will appear as fluorophore mixtures, e.g. probe 4 (fluorescein and rhodamine); probe 5 (fluorescein and CASCADE BLUE); probe 6 (rhodamine and CASCADE BLUE); and probe 7 (fluorescein, rhodamine and CASCADE BLUE).

The second way is to label each nucleic acid probe with a luminophore with distinct spectral properties. Similar conjugates can be synthesized from this invention and used in a multicolor multisequence analysis approach.

The reporter compounds of the invention can also be used for screening assays for a combinatorial library of compounds. The compounds can be screened for a number of characteristics, including their specificity and avidity for a particular recognition moiety.

Assays for screening a library of compounds are well known. A screening assay is used to determine compounds that bind to a target molecule, and thereby create a signal change which is generated by a labeled ligand bound to the target molecule. Such assays allow screening of compounds that act as agonists or antagonists of a receptor, or that disrupt a protein-protein interaction. It also can be used to detect hybridization pr binding of DNA and/or RNA.

Other screening assays are based on compounds that affect the enzyme activity. For such purposes, quenched enzyme substrates of the invention could be used to trace the interaction with the substrate. In this approach, the cleavage of the fluorescent substrate leads to a change in the spectral properties such as the excitation and emission maxima, intensity and/or lifetime, which allows to distinguish between the free and the bound luminophore.

The reporter compounds disclosed above may also be relevant to single molecule fluorescence microscopy (SMFM) where detection of single probe molecules depends on the availability of a fluorophore with high fluorescence yield, high photostability, and long excitation wavelength.

The dye compounds are also useful for use as biological stains. The dyes are not harmful and are not-toxic to cells and other biological components. There may be limitations in some instances to the use of the above compounds as labels. For example, typically only a limited number of dyes may be attached to a biomolecules without altering the fluorescence properties of the dyes (e.g. quantum yields, lifetime, emission characteristics, etc.) and/or the biological activity of the bioconjugate. Typically quantum yields may be reduced at higher degrees of labeling. Encapsulation into beads offers a means to overcome the above limitation for the use of such compounds as fluorescent markers. Fluorescent beads and polymeric materials are becoming increasingly attractive as labels and materials for bioanalytical and sensing applications. Various companies offer particles with defined sizes ranging from nanometers to micrometers. Noncovalent encapsulation in beads may be achieved by swelling the polymer in an organic solvent, such as toluene or chloroform, containing the dye. Covalent encapsulation may be achieved using appropriate reactive functional groups on both the polymer and the dyes. In general, hydrophobic versions of the invention may be used for non-covalent encapsulation in polymers, and one or more dyes could be introduced at the same time. Surface-reactive fluorescent particles allow covalent attachment to molecules of biological interest, such as antigens, antibodies, receptors etc.

Compounds of this invention may also be attached to the surface of metallic nanoparticles such as gold or silver nanoparticles. It has recently been demonstrated that fluorescent molecules may show increased quantum yields near metallic nanostructures e.g. gold or silver nanoparticles (O. Kulakovich et al. Nanoletters 2 (12) 1449-52, 2002). This enhanced fluorescence may be attributable to the presence of a locally enhanced electromagnetic field around metal nanostructures. The changes in the photophysical properties of a fluorophore in the vicinity of the metal surface may be used to develop novel assays and sensors. In one example the nanoparticle may be labeled with one member of a specific binding pair (antibody, protein, receptor etc) and the complementary member (antigen, ligand) may be labeled with a fluorescent molecule in such a way that the interaction of both binding partners leads to an detectable change in one or more fluorescence properties (such as intensity, quantum yield, lifetime, polarization, among others). Replacement of the labeled binding partner from the metal surface may lead to a change in fluorescence, that can then be used to detect and/or quantify an analyte.

Gold colloids can be synthesized by citrate reduction of a diluted aqueous $HAuCl_4$ solution. These gold nanoparticles are negatively charged due to chemisorption of citrate ions. Surface functionalization may be achieved by reacting the nanoparticles with thiolated linker groups containing amino or carboxy functions. In another approach, thiolated biomolecules are used directly for coupling to these particles.

In recent studies (T. Fare et al., *Anal. Chem.* 75(17), 4672-4675, 2003) researchers made an observation that the fluorescence signals of cyanine dyes such as CY5 dye and the ALEXA 647 dyes in microarrays are strongly dependent on the concentration of ozone during posthybridization array washing. Controlled exposures of microarrays to ozone confirmed this factor as the root cause, and showed the susceptibility of a class of cyanine dyes (e.g., CY5 dyes, ALEXA 647 dyes) to ozone levels as low as 5-10 ppb for periods as short as 10-30 s.

One of the significant findings was the low dose level (ozone concentration multiplied by exposure time) that could induce the onset of the phenomenon, suggesting many labs may be at risk. For example, it is not uncommon that the environmental ozone levels would exceed 60 ppb during peak traffic hours on a sunny summer afternoon. Reporter compounds present on or in arrays that are exposed to these levels for as short as 1 min may begin to show significant degradation in a typical laboratory setting.

There are ways that help to eliminate the occurrence of ozone effects on microarrays, for example equipping laboratories with HVAC systems having filters to significantly reduce ozone levels, or the use of dye-protecting solutions to avoid signal degradation. However, each of these approaches may add additional costs and/or time to perform the assay. These findings suggest the need for dyes and labels in the 600 to 700 nm wavelength range with improved chemical and photochemical stability.

Experimental data on squaraine dyes indicate that introduction of electron-withdrawing groups into the dye backbone may increase the photostability of such dyes. In addition it has been found that ring-substitution of squaraine dyes in the central squaraine ring with electron-withdrawing groups may lead to dyes with exceptional phtotostabilities.

Analytes

The invention may be used to detect an analyte that interacts with a recognition moiety in a detectable manner. As such, the invention can be attached to a recognition moiety which is known to those of skill in the art. Such recognition moieties allow the detection of specific analytes. Examples are pH-, or potassium sensing molecules, e.g., synthesized by introduction of potassium chelators such as crown-ethers (aza crowns, thia crowns etc). Calcium-sensors based on the BAPTA (1,2-Bis(2-aminophenoxy)ethan-N,N,N', N'-tetra-aceticacic)chelating moiety are frequently used to trace intracellular ion concentrations. The combination of a compound of the invention and the calcium-binding moiety BAPTA may lead to new long-wavelength absorbing and emitting Ca-sensors which could be used for determination of intra- and extracellular calcium concentrations (Akkaya et al. Tetrahedron Lett. 38:4513-4516 (1997). Additionally, or in the alternative, reporter compounds already having a plurality of carboxyl functional groups, as shown in Example 15, may be directly used for sensing and/or quantifying physiologically and environmentally relevant ions.

The NH-substituted dyes of this invention are pH sensitive and can in particular be valuable for the assessment of the intracellular pH and for other applications where the local pH of the environment changes e.g. cell-based measurements of G-protein coupled receptors as described in M. E. Cooper et al. J. Chem. Soc. Chem. Commun. 2000, 2323-2324. The water-soluble dyes may be used directly or the reactive pH-sensitive dyes of the invention are associated with specific biomolecules which bind to certain domains in cells thus enabling the pH of only that specific environment to be assessed. While the dioxo-squaraines have pKa values in the basic pH range (pKa>8,5), (Miltsov et al., Tetrahedron Lett. 40, 4067-68, 1999), the pka's of ring-substituted versions like the dicyano-methylene derivatives (e.g. compound 16) may be closer to the physiological pH range (FIG. 4), which makes them in particular useful for such measurements. It is understood that the dyes pKa can be tuned to cover a broad pH-range by variation of the substituents on the heterocyclic bases as well as on the squaraine bridge.

Fluorescence Methods

The disclosed reporter compounds may be detected using common intensity-based fluorescence methods. The squaraine dyes are known to have lifetimes in the range of hundreds of ps to a few ns (see Example 16). The nanosecond lifetime and long-wavelength absorption and emission of these dyes when bound to proteins may allow them to be measured using relatively inexpensive instrumentation that employs laser diodes for excitation and avalanche photodiodes for detection. Typical assays based on the measurement of the fluorescence lifetime as a parameter include for example FRET (fluorescence resonance energy transfer) assays. The binding between a fluorescent donor labeled species (typically an antigen) and a fluorescent acceptor labeled species may be accompanied by a change in the intensity and the fluorescence lifetime. The lifetime can be measured using intensity- or phase-modulation-based methods (J. R. LAKOWICZ, PRINCIPLES OF FLUORESCENCE SPECTROSCOPY ($2^{nd}$ Ed. 1999)).

The dyes of this invention exhibit high intrinsic polarization in the absence of rotational motion, making them useful as tracers in fluorescence polarization (FP) assays. Fluorescence polarization immunoassays (FPI) are widely applied to quantify low molecular weight antigens. The assays are based on polarization measurements of antigens labeled with fluorescent probes. The requirement for polarization probes used in FPIs is that emission from the unbound labeled antigen be depolarized and increase upon binding to the antibody. Low molecular weight species labeled with the compounds of the invention can be used in such binding assays, and the unknown analyte concentration can determined by the change in polarized emission from the fluorescent tracer molecule. The fact that the fluorescence lifetime of compounds 15 and 16 is in the order of 1 to 2 ns makes these labels particularly useful as labels in polarization measurements of small molecular-weight antigens.

Compositions and Kits

The invention also provides compositions, kits and integrated systems for practicing the various aspects and embodiments of the invention, including producing the novel compounds and practicing of assays. Such kits and systems may include a reporter compound as described above, and may optionally include one or more of solvents, buffers, calibration standards, enzymes, enzyme substrates, and additional reporter compounds having similar or distinctly different optical properties.

Although the invention has been disclosed in preferred forms, the specific embodiments thereof as disclosed and illustrated herein are not to be considered in a limiting sense, because numerous variations are possible. Applicant regards the subject matter of his invention to include all novel and nonobvious combinations and subcombinations of the various elements, features, functions, and/or properties disclosed herein. No single element, feature, function, or property of the disclosed embodiments is essential. The following claims define certain combinations and subcombinations of elements, features, functions, and/or properties that are regarded as novel and nonobvious. Other combinations and subcombinations may be claimed through amendment of the present claims or presentation of new claims in this or a related application. Such claims, whether they are broader, narrower, or equal in scope to the original claims, also are regarded as included within the subject matter of applicant's invention.

We claim:

1. A composition of matter comprising a reporter compound, the reporter compound having a four-, five-, or six-member aromatic ring Z, with substituents A, B, C, D, E, and F, according to the formula:

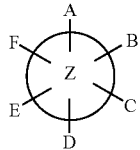

wherein F is absent when Z is a five-member ring, and wherein E and F are absent when Z is a four-member ring;

wherein A, B, C, D, E, and F may be present in any order, provided that B and C are adjacent, in which case each of A, D, E, and F is neutral, or provided that B and C are separated by one of A, D, E, or F, in which case one of A, D, E, and F is negatively charged;

when the A substituent is neutral, A is selected from the group consisting of =O, =S, =Se, =Te, =N—$R^a$, and =C($R^b$)($R^c$);

when the A substituent is negatively charged, A is —O⁻, —S⁻, —Se⁻, —Te⁻, —(N—$R^a$)⁻, and —(C($R^b$)($R^c$))⁻;

each B and C substituent is selected from the group consisting of $W^1$ and $W^2$, wherein $W^1$ and $W^2$ have the respective formulae

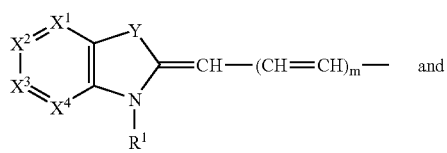

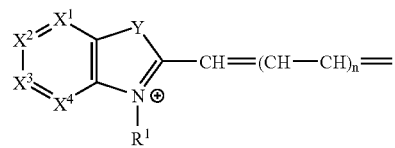

where each B and C substituent is $W^1$ if B and C are adjacent on Z, and one of B and C is $W^1$ and the other of B and C is $W^2$ if B and C are separated by one of A, D, E, and F on ring Z;

each D, E, and F substituent, when present and neutral, is independently selected from the group consisting of =O, =S, =Se, =Te, =N—$R^a$, and =C($R^b$)($R^c$); D, E, and F, when present and negatively charged, are independently selected from the group consisting of —O⁻, —S⁻, —Se⁻, —Te⁻, —(N—$R^a$)⁻, and —(C($R^b$)($R^c$))⁻;

each $R^a$ may be independently selected from the group consisting of H, aliphatic, aromatic, alicyclic, aryl-alkyl, linked carriers, reactive and reactive aliphatic substituents, —COOH, —CN, —OH, —$SO_3H$, —$SO_3R^m$, —$PO_3H_2$, —O—$PO_3H_2$, —$PO_3R_2^m$, —O—$PO_3R_2^m$, —$CONHR^m$, —$CONH_2$, COO—NHS and COO—$R^m$; each aliphatic residue may incorporate up to six heteroatoms selected from N, O, S, and can be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium; $R^m$ is selected from a group consisting of aliphatic groups, —$(CH_2)_y$—$S_c$, —$(CH_2)_y$—$R^x$, —$(CH_2)_y$—$R^±$, where y is 1 to 20, and aromatic substituents;

each $R^b$ and $R^c$ may be independently selected from the group consisting of H, aliphatic, aromatic, alicyclic, aryl-alkyl, -L-$S_c$, -L-$R^x$, -L-$R^±$, —COOH, —CN, —OH, —$SO_3H$, —$PO_3H_2$, —O—$PO_3H_2$, —$PO_3R_2^m$, —O—$PO_3R_2^m$, —$CONHR^m$, —$CONH_2$, COO—NHS and COO—$R^m$; each aliphatic residue may incorporate up to six heteroatoms selected from N, O, S, and can be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium; $R^m$ is selected from a group consisting of aliphatic groups, —$(CH_2)_y$—$S_c$, —$(CH_2)_y$—$R^x$, —$(CH_2)_y$—$R^±$, —$(CH_2)_y$—O—$(CH_2)_y$—$S_c$, —$(CH_2)_y$—O—$(CH_2)_y$—$R^x$, —$(CH_2)_y$—O—$(CH_2)_y$—$R^±$, where y is 1 to 20, and aromatic substituents;

or $R^b$ and $R^c$, taken in combination, form a cyclic or heterocyclic ring structure which is optionally substituted by -L-$S_c$, -L-$R^x$ or -L-$R^±$;

L is a covalent linkage that is linear or branched, cyclic or heterocyclic, saturated or unsaturated, having 1-20 non-hydrogen atoms from the group of C, N, P, O and S, in such a way that the linkage contains any combination of ether, thioether, amine, ester, amide bonds; single, double, triple or aromatic carbon-carbon bonds; or carbon-sulfur bonds, carbon-nitrogen bonds, phosphorus-sulfur, nitrogen-nitrogen, nitrogen-oxygen or nitrogen-platinum bonds, or aromatic or heteroaromatic bonds;

$R^x$ is a reactive group;

$S_c$ is a conjugated substance;

$R^±$ is an ionic group;

m and n are independently selected from the group consisting of 0, 1, and 2;

Y is independently selected for $W^1$ and $W^2$ from the group consisting of O, S, N—$R^d$, $CR^e$=$CR^f$ and C($R^i$)($R^j$), wherein $R^d$ is selected from the group consisting of H, aliphatic groups, alicyclic groups, aromatic groups, -L-

$S_c$, -L-$R^x$, -L-$R^±$, —$CH_2$—CONH—$SO_2$-Me; and $R^e$, $R^f$, $R^i$ and $R^j$ are selected from the group consisting of H, aliphatic groups, alicyclic groups, aromatic groups, -L-$S_c$, -L-$R^x$, -L-$R^±$, —$R^x$, —$R^±$, —$CH_2$—CONH—$SO_2$-Me, —COOH, —CN, —OH, —$SO_3H$, —$PO_3H_2$, —O—$PO_3H_2$, —$PO_3R_2^m$, —O—$PO_3R_2^m$, —CONH$R^m$, —$CONH_2$, COO—NHS and COO—$R^m$; each aliphatic residue may incorporate up to six heteroatoms selected from N, O, S, and can be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium; $R^m$ is selected from a group consisting of aliphatic groups, —$(CH_2)_y$—$S_c$, —$(CH_2)_y$—$R^x$, —$(CH_2)_y$—$R^±$, —$(CH_2)_y$—O—$(CH_2)_y$—$S_c$, —$(CH_2)_y$—O—$(CH_2)_y$—$R^x$, —$(CH_2)_y$—O—$(CH_2)_y$—$R^±$, where y is 1 to 20, and aromatic substituents; or $R^i$ and $R^j$ taken in combination form a ring-system that is optionally further substituted by one or more reactive or ionic substituents;

each $R^1$ is independently selected from H, aliphatic groups, alicyclic groups, alkylaryl groups, aromatic groups, -L-$S_c$, -L-$R^x$, -L-$R^±$, —$CH_2$—CONH—$SO_2$-Me; each aliphatic residue may incorporate up to six heteroatoms selected from N, O, S, and can be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium; provided that at least one $R^1$ is H;

each of $X^1$, $X^2$, $X^3$, and $X^4$ are independently selected from the group consisting of N, $NR^t$, O, S, and C—$R^\tau$, where $R^t$ is hydrogen, alkyl, arylalkyl and aryl groups, -L-$S_c$, -L-$R^x$, -L-$R^±$, —$CH_2$—CONH—$SO_2$-Me, where each aliphatic residue may incorporate up to six heteroatoms selected from N, O, S, and can be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium;

$R^\tau$ is hydrogen, -L-$S_c$, -L-$R^x$, -L-$R^±$, —$R^x$, —$R^±$, —$CH_2$—CONH—$SO_2$-Me, amino, alkylamino, dialkylamino, trialkylammonium, sulfo, trifluoromethyl, alkoxy, halogen, carboxy, hydroxy, phosphate, sulfate or an aliphatic, alicyclic, or aromatic group; each aliphatic residue may incorporate up to six heteroatoms selected from N, O, S, and can be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium;

adjacent $R^t$ and/or $R^\tau$ substituents, taken in combination, form a fused aromatic or heterocyclic ring that is itself optionally further substituted by H, alkyl, aryl, cycloalkyl L-$S_c$, L-$R^x$, L-$R^±$, —$R^x$ or —$R^±$; and each H may be independently replaced by a fluorine.

2. The composition of claim 1 where both $R^1$ are H.

3. The composition of claim 1, wherein Z is based on squaric acid, croconic acid, or rhodizonic acid.

4. The composition of claim 1, wherein at least one substituent of Z includes a reactive group $R^x$.

5. The composition of claim 4, wherein the reactive group $R^x$ is selected for reacting with amine moieties from the group consisting of N-hydroxysuccinimide esters, isothiocyanates, and sulfonylhalogenides.

6. The composition of claim 4, wherein the reactive group $R^x$ is selected for reacting with thiol moieties from the group consisting of iodoacetamides and maleimides.

7. The composition of claim 4, wherein the reactive group $R^x$ is selected for reacting with nucleic acids from the group consisting of phosphoramidites.

8. The composition of claim 1, wherein at least one substituent of Z includes a linked carrier L-$S_c$.

9. The composition of claim 8, wherein the carrier $S_c$ is selected from the group consisting of proteins, DNA, polypeptides, polynucleotides, beads, microplate well surfaces, small-molecule drugs, lectins, pharmacological agents and metallic nanoparticles.

10. The composition of claim 9, wherein the carrier $S_c$ is a polypeptide or a polynucleotide.

11. The composition of claim 1, further comprising a carrier $S_c$, which is associated covalently with the reporter compound through reaction with a reactive group on at least one substituent of Z.

12. The composition of claim 1, wherein at least one substituent of Z is n substituent $R^±$ capable of increasing the hydrophilicity of the entire photoluminescent compound.

13. The composition of claim 12, wherein the $R^±$ substituent is selected from the group consisting of —$CH_2$—CONH—$SO_2$-Me, $SO_3^-$, $COO^-$, $PO_3^{2-}$, O—$PO_3^{2-}$, $PO_3R^-$, O—$PO_3R^-$ and $N(R^I)_3^+$, wherein R and $R^I$ are independently an aliphatic or aromatic moiety.

14. The composition of claim 1, wherein the substituents of Z are selected so that the reporter compound is electrically neutral, increasing its hydrophobicity.

15. The composition of claim 1, wherein the substituents of Z are selected so that the reporter compound contains a maximal positive or negative net charge thereby maximizing its solubility in aqueous media and reducing its aggregation tendency in water and when covalently bound to proteins or other biomolecules.

16. The composition of claim 1, wherein the reporter compound is capable of covalently reacting with at least one of biological cells, DNA, lipids, nucleotides, polymers, proteins, lectins, pharmacological agents and solid surfaces.

17. The composition of claim 1, wherein the reporter compound is covalently or noncovalently associated with at least one of biological cells, DNA, lipids, nucleotides, polymers, proteins, and pharmacological agents.

18. The composition of claim 1, wherein both m and n are 0.

19. The composition of claim 1, wherein B and C are adjacent, and are linked to Z through a 1,2-linkage.

20. The composition of claim 1, wherein B and C are separated by one of A, D, E, or F, and are linked to Z through a 1,3-linkage.

21. The composition of claim 1, further comprising a second reporter compound selected from the group consisting of luminophores and chromophores.

22. The composition of claim 21, wherein one of the reporter compound and the second reporter compound is an energy transfer donor and the other is an energy transfer acceptor.

23. The composition of claim 1, wherein the reporter compound may be induced to luminesce by exposing the reporter compound to one or more of the following: electromagnetic energy, chemical energy, and electrochemical energy.

24. A compound having the formula

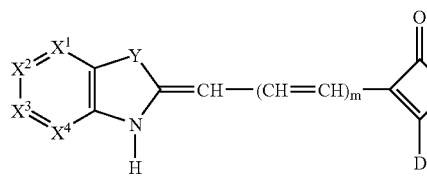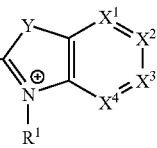

wherein D is —O⁻, —S⁻, —Se⁻, —Te⁻, —(N—R$^a$)⁻, and —(C(R$^b$)(R$^c$))⁻), wherein R$^a$, R$^b$ and R$^c$ may be selected from the group consisting of H, aliphatic, aromatic, alicyclic, arylalkyl, -L-S$_c$, -L-R$^x$, -L-R$^±$, —COOH, —CN, —OH, —SO$_3$H, —PO$_3$H$_2$, —O—PO$_3$H$_2$, —PO$_3$R$_2{}^m$, —O—PO$_3$R$_2{}^m$, —CONHR$^m$, —CONH$_2$, COO—NHS and COO—R$^m$; each aliphatic residue may incorporate up to six heteroatoms selected from N, O, S, and can be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium; R$^m$ is selected from a group consisting of -L-S$_c$, -L-R$^x$, -L-R$^±$, aliphatic substituents and aromatic substituents; or R$^b$ and R$^c$, taken in combination, form a cyclic or heterocyclic ring structure;

L is —(CH$_2$)$_o$(CONH(CH$_2$)$_p$—)$_q$ where o is 1 to 5, p is 1 to 5 and q is 0 or 1, or a polyether linkage;

R$^x$ is selected from carboxylic acid, succinimidyl ester, maleimide, iodoacetamide, sulfonyl chloride or phosphoramidite;

R$^±$ is selected from the group of sulfate, sulfonate, phosphate, phosphonate or trialkylammonium;

S$_c$ is a conjugated substance that is an antibody or fragment thereof, a protein, a peptide, DNA, a nucleotide, biotin, a drug molecule, a hormone, a solid surface or a lectin;

m and n are independently selected from the group consisting of 0, 1, and 2;

Y is independently selected from the group consisting of O, S, N—R$^d$, CR$^e$=CR$^f$ and C(R$^i$)(R$^j$), wherein R$^d$ is selected from the group consisting of H, aliphatic groups, alicyclic groups, aromatic groups, -L-S$_c$, -L-R$^x$, -L-R$^±$, —CH$_2$—CONH—SO$_2$-Me; R$^e$, R$^f$, R$^i$ and R$^j$ are selected from the group consisting of H, aliphatic groups, alicyclic groups, aromatic groups, -L-S$_c$, -L-R$^x$, -L-R$^±$, —CH$_2$—CONH—SO$_2$-Me, —COOH, —CN, —OH, —SO$_3$H, —PO$_3$H$_2$, —O—PO$_3$H$_2$, —PO$_3$R$_2{}^m$, —O—PO$_3$R$_2{}^m$, —CONHR$^m$, —CONH$_2$, COO—NHS and COO—R$^m$; each aliphatic residue may incorporate up to six heteroatoms selected from N, O, S, and can be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium; R$^m$ is selected from a group consisting of -L-S$_c$, -L-R$^x$, -L-R$^±$, aliphatic and aromatic substituents; or R$^i$ and R$^j$ taken in combination form a ring-system that is optionally further substituted by one or more reactive or ionic substituents;

R$^1$ is selected from H, aliphatic groups, alicyclic groups, alkylaryl groups, aromatic groups, -L-S$_c$, -L-R$^x$, -L-R$^±$, —CH$_2$—CONH—SO$_2$-Me; each aliphatic residue may incorporate up to six heteroatoms selected from N, O, S, and can be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium;

each of X$^1$, X$^2$, X$^3$, and X$^4$ are independently selected from the group consisting of N, NR$^t$, O, S, and C—R$^τ$, where R$^t$ is hydrogen, alkyl, arylalkyl and aryl groups, -L-S$_c$, -L-R$^x$, -L-R$^±$, —CH$_2$—CONH—SO$_2$-Me; each aliphatic residue may incorporate up to six heteroatoms selected from N, O, S, and can be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium; R$^τ$ is hydrogen, aliphatic, alicyclic, aromatic group, -L-S$_c$, -L-R$^x$, -L-R$^±$, —CH$_2$—CONH—SO$_2$-Me, F, Cl, Br, I, alkoxy, amino, sulfate, trifluoromethyl, nitro, azido, alkyl-amino, dialkyl-amino or trialkylammonium, —COOH, —CN, —OH, —SO$_3$H, —PO$_3$H$_2$, —O—PO$_3$H$_2$, —PO$_3$R$_2{}^m$, —O—PO$_3$R$_2{}^m$, —CONHR$^m$, —CONH$_2$, COO—NHS and COO—R$^m$; each aliphatic residue may incorporate up to six heteroatoms selected from N, O, S, and can be substituted one or more times by F, Cl, Br, I, hydroxy, alkoxy, carboxy, sulfo, phosphate, amino, sulfate, phosphonate, trifluoromethyl, cyano, nitro, azido, alkyl-amino, dialkyl-amino or trialkylammonium; R$^m$ is selected from a group consisting of -L-S$_c$, -L-R$^x$, -L-R$^±$, aliphatic and aromatic substituents; adjacent R$^t$ and/or R$^τ$ substituents, taken in combination, form a fused aromatic or heterocyclic ring that is itself optionally further substituted by H, alkyl, aryl, cycloalkyl, -L-S$_c$, -L-R$^x$, L-R$^±$, —R$^x$, —R$^±$;

each H may be independently replaced by a fluorine.

25. A compound having the formula

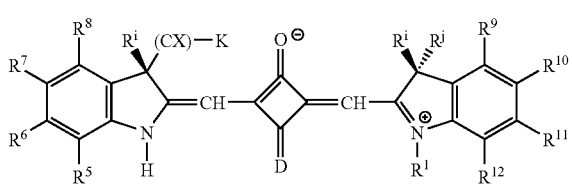

where D is =O, =S, =N(R$^a$), and =C(R$^b$)(R$^c$); R$^a$=H, —OH, —CN, —COOH; R$^b$ and R$^c$ are independently selected from H, —COOH, —PO$_3$H$_2$, —CN, —SO$_3$H, —COO—R$^m$, —CONHR$^m$ where R$^m$ is selected from a group consisting of -L-S$_c$, -L-R$^x$, -L-R$^±$, aliphatic and aromatic substituents; or R$^b$ and R$^c$, taken in combination, may form a cyclic or heterocyclic ring structure;

R$^i$ and R$^j$ are selected from the group consisting of H, aliphatic groups, alicyclic groups, aromatic groups, -L-S$_c$, -L-R$^x$, -L-R$^±$, —CH$_2$—CONH—SO$_2$-Me, COOH, —CN, —OH, —SO$_3$H, —PO$_3$H$_2$, —O—PO$_3$H$_2$, —PO3R$_2^m$, —O—PO$_3$R$_2^m$, —CONHR$^m$, —CONH$_2$, COO—NHS and COO—R$^m$; R$^i$ and R$^j$ taken in combination form a ring-system that is optionally further substituted by one or more reactive or ionic substituents;

L=—(CH$_2$)$_o$(CONH(CH$_2$)$_p$—)$_q$ where o is 1 to 5, p is 1 to 5 and q is 0 or 1;

R$^x$ is selected from carboxylic acid, succinimidyl ester, maleimide, iodoacetamide, sulfonyl chloride, or phosphoramidite;

R$^±$ is selected from the group of sulfate, sulfonate, phosphate, phosphonate or trialkylammonium;

S$_c$ is a conjugated substance that is an antibody or fragment thereof, a protein, a peptide, DNA, a nucleotide, biotin, a drug molecule, a hormone, a solid surface or a lectin;

R$^1$ is selected from H, aliphatic groups, alicyclic groups, alkylaryl groups, aromatic groups, -L-S$_c$, -L-R$^x$, -L-R$^±$, —CH$_2$—CONH—SO$_2$-Me;

R$^5$—R$^{12}$ is selected from H, aliphatic groups, aromatic groups, -L-S$_c$, -L-R$^x$, -L-R$^±$, —R$^x$, —R$^±$, —CH$_2$—CONH—SO$_2$-Me, amino, alkylamino, dialkylamino, and halogen; adjacent R$^5$—R$^{12}$ substituents, taken in combination, may form a fused aromatic or heterocyclic ring that is itself optionally further substituted by H, -L-S$_c$, -L-R$^x$, -L-R$^±$, —R$_x$ and —R$^±$;

(CX) is a single covalent bond, —CH$_2$—CONH—SO$_2$—CH$_2$—, an aliphatic group, an alicyclic group, or -L-; and K is COOH, N-hydroxy succinimide, iodoacetamide, maleimide, sulfonylchloride, phosphoramidite, —SO$_3^-$, —PO$_3^{2-}$, —O—PO$_3^{2-}$, —OH, or —NH$_2$ or —N(R$^I$)$_3^+$, where R$^I$ is selected from aliphatic and aromatic residues.

26. A compound having the formula

R$^1$ is selected from H, aliphatic groups, -L-S$_c$, -L-R$^x$, -L-R$^±$, —CH$_2$—CONH—SO$_2$-Me;

R$^i$ and R$^j$ are selected from the group consisting of H, CH$_3$, COOH, -L-S$_c$, -L-R$^x$, L-R$^±$, —R$^±$, —(CH$_2$)$_r$—CONH—SO$_2$-Me, where r=0-5;

L=—(CH$_2$)$_o$(CONH(CH$_2$)$_p$)$_q$ where o is 1-5, p is 1-5 and q is 0 or 1;

R$^x$ is a reactive group such as a carboxylic acid, a succinimidyl ester, a maleimide, an iodoacetamide, or a phosphoramidite, R$^±$ is selected from the group of sulfate, sulfonate, phosphate, phosphonate and quaternary ammonium —N(R$^I$)$_3^+$, where R$^I$ is methyl or ethyl, S$_c$ is a conjugated substance that is an antibody or fragment thereof, a protein, a peptide, DNA, a nucleotide, biotin, a drug molecule, a hormone, or a lectin.

27. A compound having the formula

R$^1$ is selected from H, aliphatic groups, -L-S$_c$, -L-R$^x$, -L-R$^±$, —CH$_2$—CONH—SO$_2$-Me;

R$^i$ and R$^j$ are selected from the group consisting of H, CH$_3$, COOH, -L-S$_c$, -L-R$^x$, L-R$^±$, —R$^±$, and —(CH$_2$)$_r$—CONH—SO$_2$-Me, where r=0-5;

L=—(CH$_2$)$_o$(CONH(CH$_2$)$_p$)$_q$ where o is 1-5, p is 1-5 and q is 0 or 1;

R$^x$ is a reactive group such as a carboxylic acid, a succinimidyl ester, a maleimide, an iodoacetamide, or a phosphoramidite, R$^±$ is selected from the group of sulfate, sulfonate, phosphate, phosphonate and quaternary ammonium —N(R$^I$)$_3^+$, where R$^I$ is methyl or ethyl, S$_c$ is a conjugated substance that is an antibody or fragment thereof, a protein, a peptide, DNA, a nucleotide, biotin, a drug molecule, a hormone, or a lectin.

28. A compound having the formula

R$^1$ and R$^a$ are selected from H, aliphatic groups, -L-S$_c$, -L-R$^x$, -L-R$^±$, —CH$_2$—CONH—SO$_2$-Me;

R$^i$ and R$^j$ are selected from the group consisting of H, CH$_3$, aliphatic, COOH, -L-S$_c$, -L-R$^x$, L-R$^±$, —R$^±$, and —(CH$_2$)$_r$—CONH—SO$_2$-Me, where r=0-5;

L=—(CH$_2$)$_o$(CONH(CH$_2$)$_p$)$_q$ where o is 1-5, p is 1-5 and q is 0 or 1;

R$^x$ is a reactive group such as a carboxylic acid, a succinimidyl ester, a maleimide, an iodoacetamide, or a phosphoramidite.

29. A compound having the formula

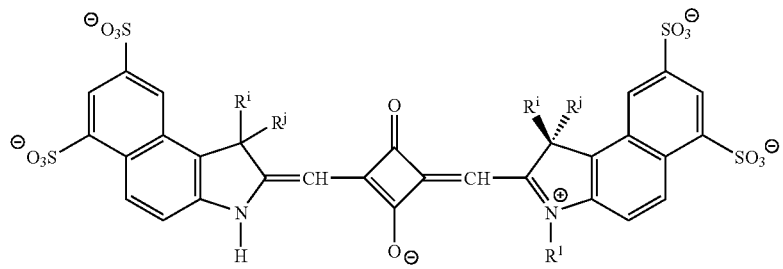

R[1] and R[a] are selected from H, aliphatic groups, -L-S_c, -L-R[x], -L-R[±], —CH_2—CONH—SO_2-Me;

R[i] and R[j] are selected from the group consisting of H, CH_3, aliphatic, COOH, -L-S_c, -L-R[x], L-R[±], —R[±], and —(CH_2)_r—CONH—SO_2-Me, where r=0-5;

L=—(CH_2)_o(CONH(CH_2)_p)_q where o is 1-5, p is 1-5 and q is 0 or 1;

R[x] is a reactive group such as a carboxylic acid, a succinimidyl ester, a maleimide, an iodoacetamide, or a phosphoramidite.

* * * * *

UNITED STATES PATENT AND TRADEMARK OFFICE
CERTIFICATE OF CORRECTION

PATENT NO.         : 7,411,068 B2                                    Page 1 of 1
APPLICATION NO. : 10/986446
DATED              : August 12, 2008
INVENTOR(S)        : Terpetschnig et al.

It is certified that error appears in the above-identified patent and that said Letters Patent is hereby corrected as shown below:

Claim 28, Column 54, lines 44 - 56, please replace chemical structure with:

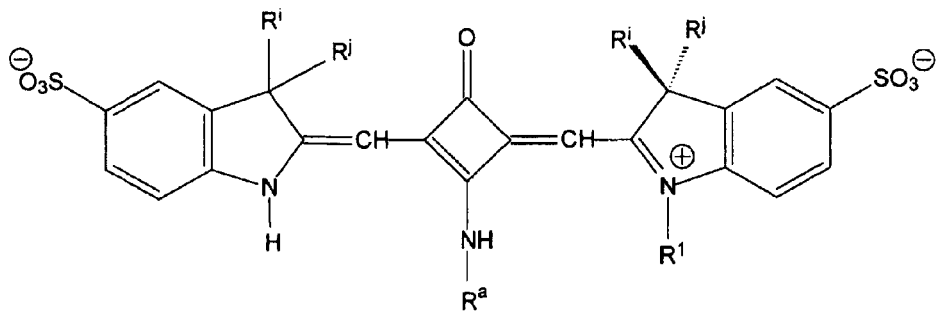

Claim 29, Column 55, lines 2 - 16, please replace chemical structure with:

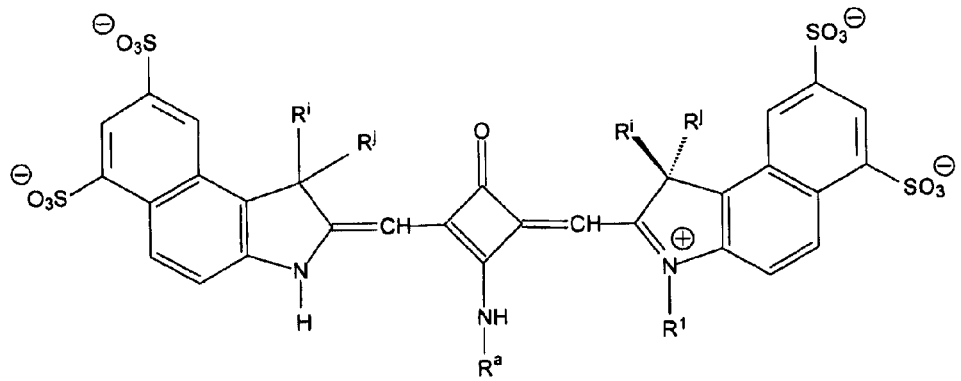

Signed and Sealed this

Tenth Day of March, 2009

JOHN DOLL
*Acting Director of the United States Patent and Trademark Office*